US009504687B2

(12) United States Patent
Xiang et al.

(10) Patent No.: US 9,504,687 B2
(45) Date of Patent: Nov. 29, 2016

(54) TREATING BAX(Δ)2-POSITIVE CANCER WITH CHEMOTHERAPIES TARGETING CASPASE 8

(71) Applicant: Mumetel, LLC, Saint Charles, IL (US)

(72) Inventors: Jialing Xiang, Chicago, IL (US); Li Ma, Chicago, IL (US)

(73) Assignee: Mumetel, LLC, Saint Charles, IL (US)

( * ) Notice: Subject to any disclaimer, the term of this patent is extended or adjusted under 35 U.S.C. 154(b) by 142 days.

(21) Appl. No.: 14/460,352

(22) Filed: Aug. 14, 2014

(65) Prior Publication Data

US 2015/0111911 A1 Apr. 23, 2015

Related U.S. Application Data

(60) Provisional application No. 61/867,012, filed on Aug. 16, 2013.

(51) Int. Cl.

| | |
|---|---|
| ***A61K 31/513*** | (2006.01) |
| ***A61K 45/06*** | (2006.01) |
| ***A61K 31/17*** | (2006.01) |

(52) U.S. Cl.

CPC ............ *A61K 31/513* (2013.01); *A61K 31/17* (2013.01)

(58) Field of Classification Search

None

See application file for complete search history.

(56) References Cited

PUBLICATIONS

Bertagnolli et al (Journal of Clinical Oncology, 2009, vol. 27, pp. 1814-1821).*

Wilson et al (Clinical Colorectal Cancer, 2007, vol. 7, suppl. 1, pp. S28-S36).*

The abstract of Zhang et al (Journal of Clinical Oncology, May 20, 2013, Suppl., e14707).*

Haferkamp, B., et al. BaxDelta2 is a Novel Bax Isoform Unique to Microsatellite Unstable Tumors. The Journal of Biological Chemistry, 2012; 287(41): 34722-34729.

Haferkamp, B., et al. BaxDelta2 Family Alternative Splicing Salvages Bax Microsatellite-Frameshift Mutations. Genes & Cancer, 2013; 4(11-12): 501-512.

Zhang, H., et al. BaxΔ2 Promotes Apoptosis through Caspase-8 Activation in Microsatellite Unstable Colon Cancer. Molecular Cancer Research, retrieved Jul. 14, 2014;12(9), 30 pages.

Oltvai, Z.N., et al. Bcl-2 Heterodimerizes In Vivo with a Conserved Homolog, Bax, That Accelerates Programmed Cell Death. Cell, Aug. 27, 1993; 74(4):609-19.

Reed, J.C. Regulation of apoptosis by bcl-2 family proteins and its role in cancer and chemoresistance. Current Opinion in Oncology. Nov. 1995;7(6):541-6.

Boldin M.P. et al. Involvement of MACH, a Novel MORT1/FADD-Interacting Protease, in Fas/APO-1- and TNF Receptor-Induced Cell Death. Cell, Jun. 14, 1996;85(6):803-15.

Stupack, D.G. Caspase-8 as a therapeutic target in cancer. Cancer Letters, May 28, 2013;332(2):133-40.

* cited by examiner

*Primary Examiner* — Karen Canella

(74) *Attorney, Agent, or Firm* — Sheppard Mullin Richter & Hampton LLP

(57) ABSTRACT

Discovery of a new Bax isoform, BaxΔ2, in cancer cell lines and primary tumors is described. The BaxΔ2 isoform resulted from combination of Bax microsatellite mutation and alternative splicing Bax exon 2. It is also discovered that BaxΔ2 renders cancer cells sensitive to certain chemotherapeutic drugs that target caspase 8. Also provided are methods for treating colorectal cancer by administering to a colorectal cancer patient a chemotherapeutic agent that is capable of activating caspase 8, wherein the patient contains a cancer cell that expresses a BaxΔ2 protein (SEQ ID NO. 2).

11 Claims, 11 Drawing Sheets

Fig. 2

SEQ ID NO: 1

5’ tcacgtgacccgggcgcgctgcggccgcccgcgcggacccggcgagaggcggcggcgggagcggcg
gtgATGGACGGGTCCGGGGAGCAGCCCAGAGGCGGGGGGTTTCATCCAG
GATCGAGCAGGGCGAATGGGGGGGAGGCACCCGAGCTGGCCCTGGACC
CGGTGCCTCAGGATGCGTCCACCAAGAAGCTGAGCGAGTGTCTCAAGCG
CATCGGGGACGAACTGGACAGTAACATGGAGCTGCAGAGGATGATTGCC
GCCGTGGACACAGACTCCCCCCGAGAGGTCTTTTTCCGAGTGGCAGCTG
ACATGTTTTCTGACGGCAACTTCAACTGGGGCCGGGTTGTCGCCCTTTTC
TACTTTGCCAGCAAACTGGTGCTCAAGGCCCTGTGCACCAAGGTGCCGG
AACTGATCAGAACCATCATGGGCTGGACATTGGACTTCCTCCGGGAGCGG
CTGTTGGGCTGGATCCAAGACCAGGGTGGTTGGGACGGCCTCCTCTCCT
ACTTTGGGACGCCCACGTGGCAGACCGTGACCATCTTTGTGGCGGGAGT
GCTCACCGCCTCACTCACCATCTGGAAGAAGATGGGCTGAggcccccagctgc
cttggactgtgtttttcctccataaattatggcatttttctgggaggggtggggattgggggacatgggcatttttctt
acttttgtaattattgggggggtgtggggaagagtggtcttgagggggtaataaacctccttcgggacacaaaa
aaaaaaaaaaaaaaaaaaaa aaaa aaaa aaaa aaaa aaaa aaaa aaaa aaaa aaaa aaaa a
aaaaaaaaaaaa 3’

Fig. 3

SEQ ID NO: 2

MDGSGEQPRGGGFHPGSSRANGGEAPELALDPVPQDASTKKLSECLKR
IGDELDSNMELQRMIAAVDTDSPREVFFRVAADMFSDGNFNWGRVVALF
YFASKLVLKALCTKVPELIRTIMGWTLDFLRERLLGWIQDQGGWDGLLSY
FGTPTWQTVTIFVAGVLTASLTIWKKMG

Fig. 4

SEQ ID NO: 3

GFHPGSSRAN

SEQUENCE LISTING

```
<160> NUMBER OF SEQ ID NOS: 47

<210> SEQ ID NO 1
<211> LENGTH: 837
<212> TYPE: DNA
<213> ORGANISM: Homo sapiens
<220> FEATURE:
<221> NAME/KEY: CDS
<222> LOCATION: (70)..(594)

<400> SEQUENCE: 1

tcacgtgacc cgggcgcgct gcggccgccc gcgcggaccc ggcgagaggc ggcggcggga      60

gcggcggtg atg gac ggg tcc ggg gag cag ccc aga ggc ggg ggg ttt cat     111
          Met Asp Gly Ser Gly Glu Gln Pro Arg Gly Gly Gly Phe His
          1               5                   10

cca gga tcg agc agg gcg aat ggg ggg gag gca ccc gag ctg gcc ctg      159
Pro Gly Ser Ser Arg Ala Asn Gly Gly Glu Ala Pro Glu Leu Ala Leu
15                  20                  25                  30

gac ccg gtg cct cag gat gcg tcc acc aag aag ctg agc gag tgt ctc      207
Asp Pro Val Pro Gln Asp Ala Ser Thr Lys Lys Leu Ser Glu Cys Leu
                35                  40                  45

aag cgc atc ggg gac gaa ctg gac agt aac atg gag ctg cag agg atg      255
Lys Arg Ile Gly Asp Glu Leu Asp Ser Asn Met Glu Leu Gln Arg Met
            50                  55                  60

att gcc gcc gtg gac aca gac tcc ccc cga gag gtc ttt ttc cga gtg      303
Ile Ala Ala Val Asp Thr Asp Ser Pro Arg Glu Val Phe Phe Arg Val
        65                  70                  75

gca gct gac atg ttt tct gac ggc aac ttc aac tgg ggc cgg gtt gtc      351
Ala Ala Asp Met Phe Ser Asp Gly Asn Phe Asn Trp Gly Arg Val Val
    80                  85                  90

gcc ctt ttc tac ttt gcc agc aaa ctg gtg ctc aag gcc ctg tgc acc      399
Ala Leu Phe Tyr Phe Ala Ser Lys Leu Val Leu Lys Ala Leu Cys Thr
95                  100                 105                 110

aag gtg ccg gaa ctg atc aga acc atc atg ggc tgg aca ttg gac ttc      447
Lys Val Pro Glu Leu Ile Arg Thr Ile Met Gly Trp Thr Leu Asp Phe
                115                 120                 125

ctc cgg gag cgg ctg ttg ggc tgg atc caa gac cag ggt ggt tgg gac      495
Leu Arg Glu Arg Leu Leu Gly Trp Ile Gln Asp Gln Gly Gly Trp Asp
            130                 135                 140

ggc ctc ctc tcc tac ttt ggg acg ccc acg tgg cag acc gtg acc atc      543
Gly Leu Leu Ser Tyr Phe Gly Thr Pro Thr Trp Gln Thr Val Thr Ile
        145                 150                 155

ttt gtg gcg gga gtg ctc acc gcc tca ctc acc atc tgg aag aag atg      591
Phe Val Ala Gly Val Leu Thr Ala Ser Leu Thr Ile Trp Lys Lys Met
    160                 165                 170

ggc tgaggccccc agctgccttg gactgtgttt ttcctccata aattatggca            644
Gly
175

tttttctggg aggggtgggg attgggggac atgggcattt ttcttacttt tgtaattatt     704

ggggggtgtg gggaagagtg gtcttgaggg ggtaataaac ctccttcggg acacaaaaaa     764

aaaaaaaaaa aaaaaaaaaa aaaaaaaaaa aaaaaaaaaa aaaaaaaaaa aaaaaaaaaa     824

aaaaaaaaaa aaa                                                        837


<210> SEQ ID NO 2
<211> LENGTH: 175
<212> TYPE: PRT
<213> ORGANISM: Homo sapiens
```

<400> SEQUENCE: 2

Met Asp Gly Ser Gly Glu Gln Pro Arg Gly Gly Gly Phe His Pro Gly
1 5 10 15

Ser Ser Arg Ala Asn Gly Gly Glu Ala Pro Glu Leu Ala Leu Asp Pro
20 25 30

Val Pro Gln Asp Ala Ser Thr Lys Lys Leu Ser Glu Cys Leu Lys Arg
35 40 45

Ile Gly Asp Glu Leu Asp Ser Asn Met Glu Leu Gln Arg Met Ile Ala
50 55 60

Ala Val Asp Thr Asp Ser Pro Arg Glu Val Phe Phe Arg Val Ala Ala
65 70 75 80

Asp Met Phe Ser Asp Gly Asn Phe Asn Trp Gly Arg Val Val Ala Leu
85 90 95

Phe Tyr Phe Ala Ser Lys Leu Val Leu Lys Ala Leu Cys Thr Lys Val
100 105 110

Pro Glu Leu Ile Arg Thr Ile Met Gly Trp Thr Leu Asp Phe Leu Arg
115 120 125

Glu Arg Leu Leu Gly Trp Ile Gln Asp Gln Gly Gly Trp Asp Gly Leu
130 135 140

Leu Ser Tyr Phe Gly Thr Pro Thr Trp Gln Thr Val Thr Ile Phe Val
145 150 155 160

Ala Gly Val Leu Thr Ala Ser Leu Thr Ile Trp Lys Lys Met Gly
165 170 175

<210> SEQ ID NO 3
<211> LENGTH: 10
<212> TYPE: PRT
<213> ORGANISM: Homo sapiens

<400> SEQUENCE: 3

Gly Phe His Pro Gly Ser Ser Arg Ala Asn
1 5 10

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Asp Glu Val Asp
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Ile Glu Thr Asp
1

<210> SEQ ID NO 6
<211> LENGTH: 4
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 6

Tyr Val Ala Asp
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Leu Glu His Asp
1

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
ccagaggcgg ggggtttcat cc 22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
cagaggcggg gggtttcatc 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
ggcggggggt ttcatccagg 20

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
ggagcagccc agaggcgggg ggttt 25

<210> SEQ ID NO 12
<211> LENGTH: 22

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
gaggcggggg gtttcatcca gg 22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
cggggggttt catccaggat 20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
gcggggggtt tcatccagga t 21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
gcagcccaga ggcgggggggt t 21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
agcccagagg cggggggttt ca 22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
gcccagaggc ggggggtttc at 22

<210> SEQ ID NO 18
<211> LENGTH: 23
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 18

ggagcagccc agaggcgggg ggt                                            23


<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

aggcgggggg tttcatccag ga                                             22


<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

cgggggtttt catccaggat                                                20


<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

gagcagggcg aatggggggg aggcacccg                                      29


<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

agaggcgggg ggtttcatcc                                                20


<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

ggatcgagca gggcgaatgg gggggaggc                                      29


<210> SEQ ID NO 24
<211> LENGTH: 23
<212> TYPE: DNA
<213> ORGANISM: Artificial Sequence
```

<220> FEATURE:
<223> OTHER INFORMATION: Description of Artificial Sequence: Synthetic
     oligonucleotide

<400> SEQUENCE: 24
aggcgggggg tttcatccag gat                                          23

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 25
gagcagggcg aatggggggg aggcacccga g                                 31

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 26
agcagcccag aggcgggg                                                18

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 27
ggagcagccc agaggcgggg tt                                           22

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 28
agcagcccag aggcggggtt tca                                          23

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 29
cagaggcggg gtttcatc                                                18

<210> SEQ ID NO 30
<211> LENGTH: 17
<212> TYPE: DNA
<213> ORGANISM: Artificial Sequence
<220> FEATURE:

-continued

<223> OTHER INFORMATION: Description of Artificial Sequence: Synthetic
oligonucleotide

<400> SEQUENCE: 30
aggcggggtt tcatcca 17

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
ggcggggttt catccaggat 20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
gaggcggggt ttcatccag 19

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
cggggtttca tccaggatcg a 21

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
ccagaggcgg ggtttcat 18

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
caggatcgag cagggcgaat ggggggggga 30

<210> SEQ ID NO 36
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 36

cggggtttca tccaggatcg                                                      20

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

gcagggcgaa tggggggggg aggcacccga gct                                       33

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

gaggcggggt ttcatccagg at                                                   22

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

gagcagggcg aatggggggg ggaggcacc                                            29

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

gagtgacacc ccgttctgat                                                      20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

actcgctcag cttcttggtg                                                      20

<210> SEQ ID NO 42
<211> LENGTH: 27
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 42

gctctagagc gcggacccgg cgagagg                                         27


<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

cgaattcccc tcaagaccac tcttccccac accc                                 34


<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

gctctagaga gcggcggtga tggacgggt                                       29


<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

ggaattccag ctgggggcct cagcccat                                        28


<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

ggttgtcgcc cttttctact ttgcca                                          26


<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47

gggcaaaagc uuacaaauau u                                               21
```

TREATING BAX(Δ)2-POSITIVE CANCER WITH CHEMOTHERAPIES TARGETING CASPASE 8

CROSS-REFERENCE TO RELATED APPLICATION

This application claims the benefit under 35 U.S.C. §119 (e) of provisional application U.S. Ser. No. 61/867,012, filed on Aug. 16, 2013. The content of this application is incorporated by reference into the present disclosure in its entirety.

STATEMENT REGARDING GOVERNMENT LICENSE RIGHTS

This invention was made with government support under CA 128114 awarded by National Institutes of Health. The United States government has certain rights in this invention.

FIELD

The present disclosure relates to methods for detection of a BaxΔ2 mutation and methods of treating cancer patient having the mutation.

BACKGROUND

Programmed cell death or apoptosis is a cellular "suicidal" program, which can remove damaged or cancerous cells from a human body and maintain normal tissue homeostasis. There are several key components regulating the death program and maintaining a good balance of cell survival verse death. The Bcl-2 family is the most well documented family that contains both pro-death and anti-death molecules. The anti-death molecule, such as Bcl-2 functions as oncogene, while pro-death molecule, such as Bax is served as a tumor suppressor. The ratio of Bcl-2 and Bax often dictates the chemo-sensitivities in cancer treatment.

The Bax gene has six exons. Exon 3 has a microsatellite consisting of a cluster of 8 guanines (G8) stretch, which is susceptible to mutation in tumors due to microsatellite instability (MSI). A single nucleotide deletion in the Bax G8 microsatellite tract, i.e., G8 to G7, causes a reading frameshift and disruption of the nature translational reading frame and premature termination of Bax protein translation. Bax is one of the first affected genes identified in MSI tumors and found in over 50% of a set of MSI colon cancer tumors. Such tumors with reading frameshift mutations of Bax are typically considered "Bax-negative".

RNA alternative splicing is a regulated process by which different form of mRNAs are generated from a single gene. Bax gene can generate several viable isoforms, which participate in apoptotic pathway. However, aberrant alternative splicing Bax exon 2 results in a disruption of Bax open reading frame and produces no functional viable Bax protein.

SUMMARY

The present disclosure describes the discovery of a new Bax isoform, BaxΔ2 (GenBank Accession #: JX524562.1) in the "Bax-negative" cancer cell lines and primary tumors, resulted from combination of Bax microsatellite mutation and alternative splicing Bax exon 2. It is also discovered that BaxΔ2 only exists in the Bax mutated cells and renders cancer cells sensitive to certain chemotherapeutic drugs that target caspase 8.

In one embodiment, the present disclosure provides a method for treating colorectal cancer, comprising administering to a colorectal cancer patient a chemotherapeutic agent that is capable of activating caspase 8, wherein the patient contains a cancer cell that expresses a BaxΔ2 protein (SEQ ID NO. 2).

In some aspects, the chemotherapeutic agent is not doxorubicin (Adriamycin).

In some aspects, the chemotherapeutic agent is an antimetabolite, such as a pyrimidine analog. Non-limiting examples of antimetabolites include 5-fluorouracil, hydroxyurea, doxifiuroidine, ftorafur, Capecitabine, tegafur, ralititrexed, nolatrexed, LY231514, ZD9331 and combination thereof.

A colorectal cancer can be colon cancer or rectal cancer, metastatic or non-metastatic.

In some aspects, the method further comprises detecting the expression of the BaxΔ2 protein in a cancer cell isolated from the patient. The detection can use an antibody having specificity to the BaxΔ2 protein, or alternatively by detecting a RNA sequence encoding the BaxΔ2 protein, such as SEQ ID NO. 1.

BRIEF DESCRIPTION OF THE DRAWINGS

FIG. 1 discloses SEQ ID NO: 3.

FIG. 2. The DNA sequence of BaxΔ2 (SEQ ID NO: 1).

FIG. 3. The amino acid sequence of BaxΔ2 (SEQ ID NO: 2).

Figure 4:
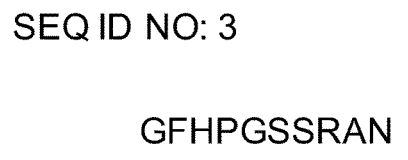

FIG. 4. The unique oligopeptide sequences of BaxΔ2 for antibody production (SEQ ID NO: 3).

DETAILED DESCRIPTION OF THE INVENTION

Definitions

Figure 1:
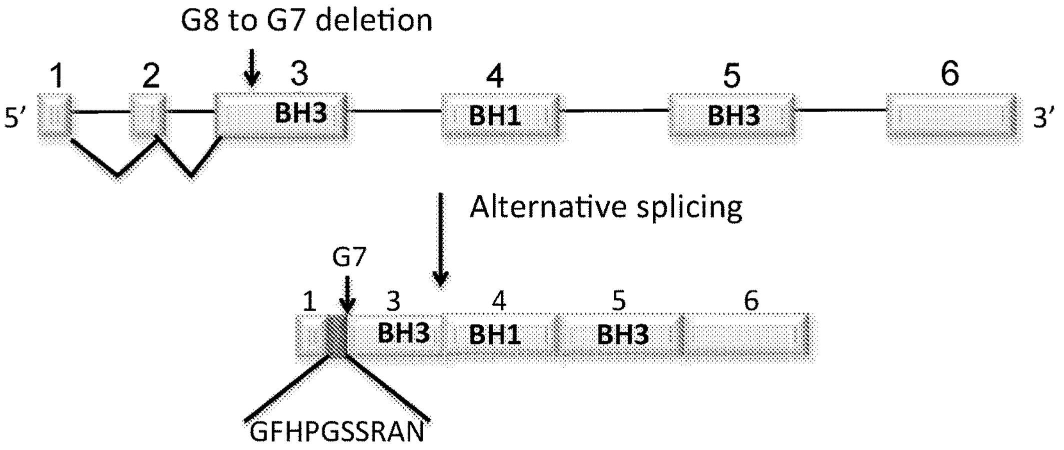
FIG. 1. Schematic illustration of production of BaxΔ2. Alternative splicing of Exon 2 (most of the exon 2 is removed but only two nucleotides left) causes a reading frameshift (grey box). The reading frame is restored at G7 microsatellite site if Bax has a mononucleotide deletion (from G8 to G7). BH, Bcl-2 homology domain.
Figure 5:
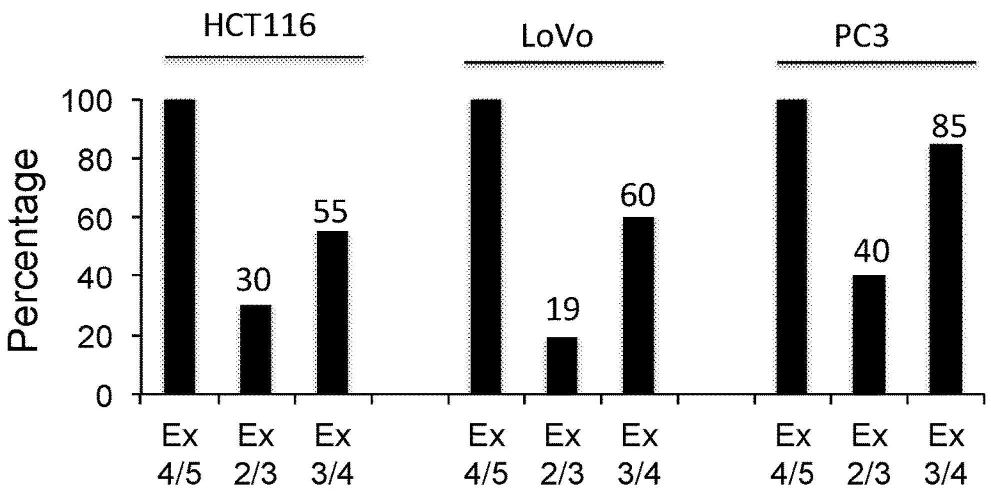
FIG. 5. Real-time PCR assay. Quantitative analysis of splicing products of Bax exons. cDNAs were generated from prostate cancer cell PC3, and colon cancer LoVo, and HCT116 cells. The product from the exon 4/5 boundary was used as normalization for comparison among the cell lines.
Figure 6:
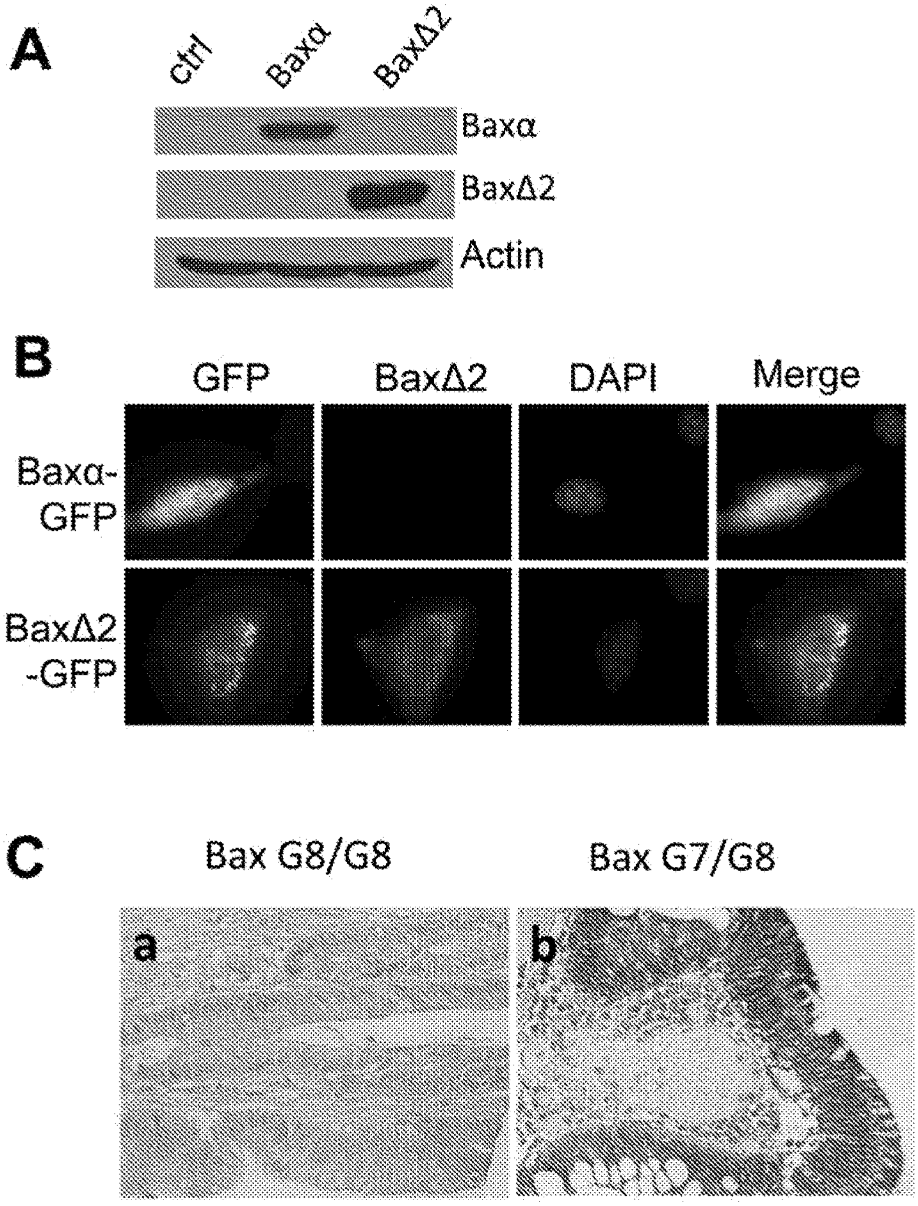
FIG. 6. Characterization of anti-BaxΔ2 antibody. A) immunoblotting analysis, Bax negative mouse embryonic fibroblast cells (bax−/− MEFs) were transfected with either BaxΔ2 or Baxα, then subjected to immunoblotting with anti-BaxΔ2 antibody (2D4) or anti-Baxα antibody (N20, Santa Cruz). B) Immunostaining bax−/− MEFs transfected with Baxα-GFP or BaxΔ2-GFP and followed by immunostaining with anti-BaxΔ2 (2D4) antibody. GFP, green fluorescence protein; nucleus stained with DAPI (4',6-diamidino-2-phenylindole). C) Immunohistochemistry of formalin-fixed paraffin embedded tissue from human colon cancer stained with anti-BaxΔ2 antibody. Slides (a) BaxΔ2 with G8 as a negative control and (b) BaxΔ2 with G7 showing positive staining.

The practice of the present invention will employ, unless otherwise indicated, conventional techniques of tissue culture, immunology, molecular biology, microbiology, cell biology and recombinant DNA, which are within the skill of the art.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. The antibodies can be polyclonal or monoclonal and can be isolated from any suitable biological source, e.g., murine, rat, sheep and canine.

The term "express" refers to the production of a gene product, such as a protein.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those skills in the art.

An "allele" refers two alternative forms of a gene that is located at same position on a specific chromosome.

A "mutation" refers to a change of DNA sequence of an organism in such a way, which may alter the genetic message carried by that gene. Example of mutation can be either removing or inserting nucleotides from DNA. Such mutation can result in alteration of reading frame or change of the nature of gene product.

A "microsatellite" refers to a short repeat nucleotide sequence, also known as simple sequence repeats (SSRs) or short tandem repeats (STRs).

A "microsatellite instability (MSI)" refers to a genetic condition with hypermutability caused by the loss of DNA mismatch repair ability. Individual with MSI has a high possibility developing cancer and other diseases (Boyer J C et al. 1995. Microsatellite instability, mismatch repair deficiency, and genetic defects in human cancer cell lines. Cancer Res 55: 6063-6070).

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence, which has a certain degree of homology with or with the complement thereof. In one aspect, homologs of nucleic acids are capable of hybridizing to the nucleic acid or complement thereof.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (1999) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/blast/Blast.cgi, last accessed on Nov. 26, 2007. Biologically equivalent polynucleotides are those having the specified percent homology and encoding a polypeptide having the same or similar biological activity.

The "alternative splicing" refers to an alternative process related to a "constitutive splicing", in which introns in pre-mRNA are removed, and remained exons are reconnected together to produce mRNA. Alternation of constitutive splicing process results in different mRNAs that may be translated to different proteins. Therefore, alternative splicing produces diversity of proteins in eukaryotes.

The term "frameshift" refers to an alteration of a reading frame for a protein translation. Alteration of the codon triplets of genetic code of messenger RNA results in different translational product or termination of translational process by a stop codon.

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences that will provide a signal upon expression of the inserted sequences, such as green fluorescent protein (GFP) and the like. The label may be detectable by itself (e.g. fluorescent labels) or, in the case of an enzymatic label, may catalyze chemical alteration of a substrate compound or composition which is detectable. The labels can be suitable for small scale detection or more suitable for high-throughput screening. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below. A peptide of three or more amino acids is commonly called an oligopeptide if the peptide chain is short. If the peptide chain is long, the peptide is commonly called a polypeptide or a protein.

A "subject" of diagnosis or treatment is a cell or a mammal, including a human. Non-human animals subject to diagnosis or treatment include, for example, murine, such as rats, mice, canine, such as dogs, leporids, such as rabbits, livestock, sport animals, and pets.

As used herein, the term "cell line" intends an immortalized population of cells is maintained in laboratory culture condition. A cell line is generally derived or selected to uniformity from tissues.

As used herein, the term "isogenic subline" intends a uniform sub-population of cells with a similar genetic background derived from a single cell in a defined cell population.

The term "polymerase chain reaction (PCR)" intends to a method as used to amplify small segments of DNA for molecular and genetic analyses. To amplify DNA, sample DNA is first heated and separates into two pieces of single-stranded DNA, and short pieces of single-stranded DNA that are complementary to the target sequence. The polymerase begins synthesizing new DNA from the end of the primer. This process results in the duplication of the original DNA and each of these strands can be used to create two new copies. At the end of the PCR reaction, the specific sequence will be accumulated. A single or a few copies of DNA is repeated as many as 30 or 40 times generating thousands to millions of copies of new DNA, which can be used for analysis, cloning, genetic engineering and sequencing.

The term "immunochemistry", as used herein, intends to a class of methods that are used for detection of targeted molecule with specific antibody based on immunological interaction between specific antigen and antibody. Such immunological approaches include but not limited to immunohistochemical staining, immunoblotting, ELISA, and immunoprecipitation known in the art for this purpose.

Chemotherapeutic agents that target caspase 8 are known in the art and can be readily tested with in vitro assays. For instance, antimetabolites increase the activity of caspase 8.

"Antimetabolites" or "antimetabolite chemotherapeutic anticancer agents" are chemicals that inhibit the use of a metabolite, which is another chemical that is part of normal metabolism. Such substances are often similar in structure to the metabolite that they interfere with, such as the antifolates that interfere with the use of folic acid.

Non-limiting examples of antimetabolites include 5-Fluorouracil (5FU), hydroxyurea, 5'-deoxy-5-fiuorouridine (doxifiuroidine), 1-tetrahydrofuranyl-5-fluorouracil (ftorafur), Capecitabine (Xeloda), S-I (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

"Pyrimidine analogs" are antimetabolites which mimic the structure of metabolic pyrimidines. Examples include 5-Fluorouracil (5FU) which inhibits thymidylate synthase, Floxuridine (FUDR), Cytarabine (Cytosine arabinoside) and 6-azauracil (6-AU).

"5-Fluorouracil" or "5-FU" is a pyrimidine analog and an antimetabolite chemotherapeutic anticancer agent. It has been in use against cancer for about 40 years, acts in several ways, but principally as a thymidylate synthase inhibitor, interrupting the action of an enzyme which is a critical factor in the synthesis of pyrimidine—which is important in DNA replication. It finds use particularly in the treatment of colorectal cancer and pancreatic cancer.

II Methods of the Invention

Nucleic Acid Based Detection

Both frameshift mutation and aberrant splicing result in disruption of Bax reading frame and no viable protein products. However, proper combinations of mutation and alternative splicing can produce a group of novel Bax isoforms. FIG. 1 illustrates the production of BaxΔ2 from alternative splicing exon 2 in combination with Bax microsatellite mononucleotide deletion G8 to G7; The DNA sequence of BaxΔ2 isoform is shown in FIG. 2. The amino acid sequence of BaxΔ2 isoform is shown in FIG. 3.

The individual carrying Bax microsatellite mutation may be detected at the genomic DNA or RNA level using a variety of techniques, which are well known in the art. The DNA or RNA samples can be obtained from tissues or cells in blood, body fluid, surgical specimen or autopsy specimens. The sample can be prepared as fresh, frozen, paraffin-embedded, or fixed with RNA-protected reagents, such as RNA later (Applied Biosystem), Trizol (Invitrogen).

The methods for preparing nucleic acids in a form that is suitable for detections of Bax microsatellite mutation and splicing variants of exon 2 are well known in the art. For example, PCR or qPCR can be performed with suitable combination of probes capable to detect any of Bax microsatellite mutations and encompass a sufficient number of nucleotides to provide a means of differentiating a wild type from mutant allele.

Probes and primers raised in accordance with the invention can be used to detect of Bax microsatellite mutation and Bax exon 2 splicing variants. The combination of the primers is enabling to quantify expression level of various Bax exon 2 splicing transcripts.

The suitable probes raised in accordance with the invention can be also used for detection of BaxΔ2 isoforms by other non-PCR based methods, such as in situ hybridization or Northern blot, in which suitable probes are only complementary to BaxΔ2 isoforms but not to wild type Bax.

The suitable probes raised in accordance with this invention can be also used to detect single-copy of BaxΔ2 RNA expression, at single-cell level, in formalin-fixed paraffin-embedded (FFPE) tissue or cells using RNA scope (Advanced Cell Diagnostics).

The oligonucleotide (probes and primers) can be chemically synthesized (Listed in Table 1) (SEQ ID NOS 8-39, respectively, in order of appearance)

TABLE 1

| Oligonucleotides for detection of BaxΔ2 isoforms | |
|---|---|
| ID | Oligonucleotides (5' to 3') |
| BD2-1 | CCAGAGGCGGGGGGTTTCATCC |
| BD2-2 | CAGAGGCGGGGGGTTTCATC |
| BD2-3 | GGCGGGGGGTTTCATCCAGG |
| BD2-4 | GGAGCAGCCCAGAGGCGGGGGGTTT |
| BD2-5 | GAGGCGGGGGGTTTCATCCAGG |
| BD2-6 | CGGGGGGTTTCATCCAGGAT |
| BD2-7 | GCGGGGGGTTTCATCCAGGAT |
| BD2-8 | GCAGCCCAGAGGCGGGGGGTT |
| BD2-9 | AGCCCAGAGGCGGGGGGTTTCA |
| BD2-10 | GCCCAGAGGCGGGGGGTTTCAT |
| BD2-11 | GGAGCAGCCCAGAGGCGGGGGGT |
| BD2-12 | AGGCGGGGGGTTTCATCCAGGA |
| BD2-13 | CGGGGGGTTTCATCCAGGAT |
| BD2-14 | GAGCAGGGCGAATGGGGGGGAGGCACCCG |
| BD2-15 | AGAGGCGGGGGGTTTCATCC |
| BD2-16 | GGATCGAGCAGGGCGAATGGGGGGGAGGC |
| BD2-17 | AGGCGGGGGGTTTCATCCAGGAT |
| BD2-18 | GAGCAGGGCGAATGGGGGGGAGGCACCCGAG |
| BG9-1 | AGCAGCCCAGAGGCGGGG |
| BG9-2 | GGAGCAGCCCAGAGGCGGGGTT |
| BG9-3 | AGCAGCCCAGAGGCGGGGTTTCA |
| BG9-4 | CAGAGGCGGGGTTTCATC |
| BG9-5 | AGGCGGGGTTTCATCCA |
| BG9-6 | GGCGGGGTTTCATCCAGGAT |
| BG9-7 | GAGGCGGGGTTTCATCCAG |
| BG9-8 | CGGGGTTTCATCCAGGATCGA |
| BG9-9 | CCAGAGGCGGGGTTTCAT |
| BG9-10 | CAGGATCGAGCAGGGCGAATGGGGGGGGA |

TABLE 1-continued

| Oligonucleotides for detection of BaxΔ2 isoforms | |
|---|---|
| ID | Oligonucleotides (5' to 3') |
| BG9-11 | CGGGGTTTCATCCAGGATCG |
| BG9-12 | GCAGGGCGAATGGGGGGGGGAGGCACCCGAGCT |
| BG9-13 | GAGGCGGGGTTTCATCCAGGAT |
| BG9-14 | GAGCAGGGCGAATGGGGGGGGGAGGCACC |

Immunochemical Detection

Antibodies generated in accordance with the invention from BaxΔ2 unique oligopeptide (SEQ ID NO: 3). Such antibodies can be used to detect and screen the presence of BaxΔ2 isoform protein products in variety of contexts by commonly used immunological based assays, which include but not limit to:

1) The antibodies can be used for the immunostaining of cells or tissues for detection of BaxΔ2 proteins. The antibodies can be also used to determine the cellular localization or tissue distribution of BaxΔ2 proteins. Immunofluorescence staining, immunohistochemical staining, or immuno-electron microscopy techniques are well known in the art can be used for this purpose.
2) The antibodies can be also used for direct or indirect enzyme-linked immnosorbent assay (ELISA) for a quantitative measurement of BaxΔ2 in certain cells or tissues. This method is more suitable, but not limited to detection of presence of BaxΔ2 proteins in cell lysate, tissue homogenate, blood, or body fluid.
3) The antibodies can be also used for immunoblotting (Western blotting) of cells and tissue to detect BaxΔ2 and distinct it from other Bax isoforms.
4) Antibodies can be used as tools for affinity purification of BaxΔ2 proteins from cells or tissues for characterization of the biological or biochemical analysis of the BaxΔ2 proteins. Methods such as affinity column chromatography with immobilized antibodies are commonly known in the art for this purpose.
5) Antibodies can be also utilized for identification of BaxΔ2 associated proteins which may involve in regulation of BaxΔ2 activity. Immunoprecipitation in conjugation with immunoblotting are commonly used for this purpose.
6) The purified/isolated BaxΔ2 proteins, in turn, can be used to detect presence of the BaxΔ2 antibodies in peripheral blood or other body fluid, or cultured cells by immuno-based methods, such ELISA assay mentioned above. The protein can be also used for in vitro drug-protein interaction during the drug screening program.

Preparation of antibodies: antibodies arised in accordance with the invention against BaxΔ2 unique oligopeptide (SEQ ID NO: 3) in the form of monoclonal antibody or polyclonal antibody for which the techniques are well established in the art of Harlow et. al. 1988. The oligopeptides can be chemically synthesized and conjugated with a certain carrier such as KLH to enhance the immunogenicity. The oligopeptides can be also designed in various lengths. The certain amino acids in the oligopeptides can be also modified chemically to mimic certain post-translational modification of the protein, such as phosphorylation, which is important for many cellular regulatory events.

In addition to oligopeptide as antigen, purified fragments or full-length BaxΔ2 isoform proteins can be also used for production of monoclonal or polyclonal antibodies.

The full-length or parts of BaxΔ2 protein can be generated from either prokaryotic or eukaryotic expression systems, such as bacteria, yeast, mammalian or other conventional recombinant DNA techniques.

The term "antibody" herein can be either monoclonal or polyclonal antibody. The antibody can be also in the form of fragments, semi-synthetic or synthetic antibody-like molecules or other forms.

Isogenic BaxΔ2 Sublines

Pared isogenic cell lines have advantage in avoiding heterogeneous genetic background, which brings complexity for result interpretation during drug screening.

Isogenic BaxΔ2 sublines contain no detectable parental Baxα protein but BaxΔ2 with different statuses. HCT116-BP10 cells are BaxΔ2 positive having both BaxΔ2 RNA and protein; HCT116-BN28 cells are BaxΔ2 negative having no BaxΔ2 RNA and protein. These sublines are a useful tool for both drug screening and biological study.

The isogenic sublines can be used for drug screening with commonly used toxicity assays, such as cell viability assay or other methods well known in the art. The sublines can be also used for identify drug or compound which is more toxic to the BaxΔ2 positive but not or less toxic to the BaxΔ2 negative cells.

The isogenic sublines can be also used for biological study to identify regulatory protein, which is presence or active in one subline but not other by subtraction library screening, RNA or protein based microarray screening. Identification of the regulatory protein can be applied for the purpose drug development.

Establishment of BaxΔ2 isogenic cell lines: The sublines can be derived from human colorectal carcinoma cell line HCT116 with ATCC accession number CCL-247, which have mixed Bax microsatellite mutation populations, 94% of BaxG7/G8, 4% of BaxG7/G7, and 2% of BaxG8/G8. Single cell cloning was carried out by serial dilution in a 96-well plate according to a standard protocol. Cells are maintained in a regular cell culture medium for 2-3 week until the single clones are expanded sufficient enough for validation. The status of Baxα and BaxΔ2 can be validated by either RNA transcript level by RT-PCR and confirmed by DNA sequence and at protein level by immunoblot analysis. The single cell derived-sublines can be individually maintained for further usage.

Methods of Treatment

The disclosure further provides methods of treating patients having a BaxΔ2-expressing cancer. The cancer can be anyone selected from a solid malignant tissue mass or tumor from the group: lung cancer, non-small cell lung cancer, breast cancer, head and neck cancer, ovarian cancer, colon cancer, rectal cancer, locally advanced rectal cancer, metastatic or non-metastatic colorectal cancer, esophageal cancer, gastric cancer, liver cancer, bone cancer, spleen cancer, pancreatic cancer, or gallbladder cancer. In one aspect, the patient suffers from colorectal cancer such as colon cancer or rectal cancer.

In another aspect of any of the above methods, uses, or therapies, the therapy is a pre-operative therapy. In another aspect, the therapy further comprises radiotherapy. In yet another aspect, the therapy is followed by surgical resection.

In some aspects, prior to the therapy, a cancer patient is screen for BaxΔ2 expression in a sample isolated from the patient. A suitable sample can be prepared from blood, plasma, a tumor cell tissue, a peripheral blood lymphocyte, or combinations thereof. The samples can be any one or more of a fixed tissue, a frozen tissue, a biopsy tissue, a resection tissue, a microdissected tissue, or combinations thereof.

The methods are useful in the assistance of an animal, a mammal or yet further a human patient. For the purpose of illustration only, a mammal includes but is not limited to a human, a simian, a murine, a bovine, an equine, a porcine or an ovine. Accordingly, a formulation comprising the necessary therapy or equivalent thereof is further provided herein. The formulation can further comprise one or more preservatives or stabilizers. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, and 1.0%).

The agents or drugs can be administered as a composition. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

Many combination chemotherapeutic regimens are known to the art, such as combinations of platinum compounds and taxanes, e.g. carboplatin/paclitaxel, capecitabine/docetaxel, the "Cooper regimen", fluorouracil-levamisole, fluorouracil-leucovorin, fluorouracil/oxaliplatin, methotrexate-leucovorin, and the like.

Combinations of chemotherapies and molecular targeted therapies, biologic therapies, and radiation therapies are also well known to the art; including therapies such as trastuzumab plus paclitaxel, alone or in further combination with platinum compounds such as oxaliplatin, for certain breast cancers, and many other such regimens for other cancers; and the "Dublin regimen" 5-fluorouracil IV over 16 hours on days 1-5 and 75 mg/m2 cisplatin IV or oxaliplatin over 8 hours on day 7, with repetition at 6 weeks, in combination with 40 Gy radiotherapy in 15 fractions over the first 3 weeks) and the "Michigan regimen" (fluorouracil plus cisplatin or oxaliplatin plus vinblastine plus radiotherapy), both for esophageal cancer, and many other such regimens for other cancers, including colorectal cancer.

In another aspect of the invention, the method for treating a patient further comprises, surgical resection of a metastatic or non-metastatic solid malignant tumor and, in some aspects, in combination with radiation. Methods for treating these tumors as Stage I, Stage II, Stage III, or Stage IV by surgical resection and/or radiation are known to one skilled in the art. Guidelines describing methods for treatment by surgical resection and/or radiation can be found at the National Comprehensive Cancer Network's web site, nccn.org, last accessed on May 27, 2008.

The invention provides an article of manufacture, comprising packaging material and at least one vial comprising a solution of the chemotherapy as described herein and/or or at least one antibody or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising the chemotherapy and/or at least one lyophilized antibody or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

Chemotherapeutic formulations of the present invention can be prepared by a process which comprises mixing at least one antibody or biological equivalent and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include those pen-injector devices for delivery of a solution such as BD Pens, BD Autojectore, Humajecti) NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic-.com; Bioject, Portland, Oreg. (available at bioject.com); National Medical Products, Weston Medical (Peterborough, UK, available at weston-medical.com), Medi-Ject Corp (Minneapolis, Minn., available at mediject.com).

Various delivery systems are known and can be used to administer a chemotherapeutic agent of the invention, e.g., encapsulation in liposomes, microparticles, microcapsules, expression by recombinant cells, receptor-mediated endocytosis. See e.g., Wu and Wu (1987) J. Biol. Chem. 262: 4429-4432 for construction of a therapeutic nucleic acid as part of a retroviral or other vector, etc. Methods of delivery include but are not limited to intra-arterial, intra-muscular, intravenous, intranasal and oral routes. In a specific embodiment, it may be desirable to administer the pharmaceutical compositions of the invention locally to the area in need of treatment; this may be achieved by, for example, and not by way of limitation, local infusion during surgery, by injection or The agents identified herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

EXAMPLES

The following examples are illustrated for the application of the invention but not intended to be limitation thereon.

Example 1

Detection of BaxΔ2 mRNA Transcripts from Tumor Cell Lines and Primary Tumors A panel of 12 cancer cell lines was examined for the Bax genomic microsatellite status and production of the BaxΔ2 transcripts. For determination of Bax MSI status, genomic DNA was isolated from each cell line using AquaPure Genomic DNA Kit (Biorad). Isolated genomic DNA was amplified by a PCR reaction using primers located in intron 2 (5'-gagtgacaccccgttctgat-3') (SEQ ID NO: 40) and in exon 3 (5'-actcgctcagcttcttggtg-3')(SEQ ID NO: 41). Amplified products were gel-extracted and sequenced for validation. The results show that Bax microsatellite stable cell lines, such as PC3 and SW1116, have BaxG8 wild type on both alleles, while Bax microsatellite unstable cell lines, such as LoVo or HCT117, have mixed G7, G8 or G9 alleles. BaxG7 was the only microsatellite sequence detected in some cells, such as 104-R, while others are heterogeneous G7 and G9, such as LoVo (Table 2).

TABLE 2

Bax microsatellite statuses and BaxΔ2 transcripts in Cancer Cell Lines

| MSI Status | Source | Organ | Bax MSI | Baxα | BaxΔ2 |
|---|---|---|---|---|---|
| Bax-MSS | PC3 | Prostate | G8 | + | − |
| | LNCaP | Prostate | G8 | + | − |
| | SW1116 | Colon | G8 | + | − |
| | HepG2 | Liver | G8 | + | − |
| Bax-MSI | DU145 | Prostate | G9 | − | − |
| | 104-S | Prostate | G7 | − | − |
| | 104-R | Prostate | G7 | − | + |
| | 104-IS | Prostate | G7 | − | + |
| | MCF-7 | Breast | G7, G8 | + | + |
| | LS174T | Colon | G7 | − | + |
| | LoVo | Colon | G7, G9 | − | + |
| | HCT116 | Colon | G7, G8 | + | + |

For detection of production of BaxΔ2 mRNA transcripts. RNA was purified from frozen cell pellets using the Purelink Micro-to-Midi Total RNA Purification System (Invitrogen) and subjected to reverse transcription polymerase chain reaction (RT-PCR). cDNA was synthesized from the RNA using the Superscript First-Strand Synthesis System for RT-PCR (Invitrogen) with oligo(dT) primers per the manufacturer's protocol. Bax mRNA isoforms were amplified using 5'-gctctagagcgcggacccggcgagagg-3' (SEQ ID NO: 42) (forward, with an Xba1 restriction site) and 5'-cgaattcccct-caagaccactcttccccacaccc-3' (SEQ ID NO: 43) (reverse, with an EcoR1 restriction site) primers with Phusion polymerase in a 35-cycle PCR: 10 sec denaturation at 95° C., 15 sec annealing at 63° C., and 20 sec extension at 72° C. The cDNA products were cloned into a standard bacterial vector, such as pBluscript, and the plasmid DNA was isolated for sequence analysis. At least 5 DNA sequences were analyzed for each cell line. Table 2 shows that none of BaxG8 cell lines produced BaxΔ2 transcript, only BaxG7 or G9 produced BaxΔ2 which was found in nearly all Bax mutated cell lines examined.

To determine whether BaxΔ2 also exists in primary tumors, Total RNA was purchased from Bioserve Biotechnologies Ltd. (Beltsville, Md.). These RNA samples were isolated from both prostate cancer and colon cancer patients (n=10 each). RT-PCR and cloning procedures were similar as that from the cell lines mentioned above. Table 3 shows that BaxΔ2 transcripts with a G7 microsatellite were found in 1 in 10 colon and 2 in 10 prostate tumors. BaxΔ2G9 was found in one in

TABLE 3

BaxΔ2 Family Transcripts in Primary Human Tumors

| Tumors | Origins | Grade | Bax MS Detected* | Baxα | BaxΔ2 | BaxΔ2 Splicing*** |
|---|---|---|---|---|---|---|
| 1 | Colon | II | G7, G8 | 16 | 1 | — |
| 2 | Colon | II | G8 | 6 | — | — |
| 3 | Colon | II | G8 | 7 | — | — |
| 4 | Colon | III | G8 | 14 | — | — |
| 5 | Colon | III | G8 | 11 | — | — |

TABLE 3-continued

BaxΔ2 Family Transcripts in Primary Human Tumors

| Tumors | Origins | Grade | Bax MS Detected* | Baxα | BaxΔ2 | BaxΔ2 Splicing*** |
|---|---|---|---|---|---|---|
| 6 | Colon | III | G8 | 7 | — | — |
| 7 | Colon | III | G8, G9 | 7 | — | — |
| 8 | Colon | IV | G8 | 14 | — | — |
| 9 | Colon | IV | G8 | 8 | — | — |
| 10 | Colon | IV | G8 | 9 | — | — |
| 11 | Prostate | III | G7, G8 | 10 | 1 | 1 |
| 12 | Prostate | III | G8 | 12 | — | — |
| 13 | Prostate | III | G7, G8 | 11 | — | 1 |
| 14 | Prostate | III | G8 | 10 | — | 1 |
| 15 | Prostate | III | G8 | 6 | — | — |
| 16 | Prostate | III | G8, G9 | 2 | — | — |
| 17 | Prostate | III | G8 | 10 | — | — |
| 18 | Prostate | IV | G8 | 7 | — | — |
| 19 | Prostate | IV | G7, G8 | 12** | — | — |
| 20 | Prostate | IV | G8 | 7 | — | — |

Note:
*Bax MS summarizes Bax microsatellite sequences detected in mRNA transcripts for each tumor sample.
**The transcripts include two sequences which have Bax G7, but Baxα constitutive splicing;
***These sequences have Bax G8, but with BaxΔ2 alternative splicing.

10 prostate tumors (Table 3). These results indicate that BaxΔ2 transcripts are produced in Bax microsatellite mutant cell lines and primary tumors.

Example 2

Quantitation of Expression Levels for Bax Exons by qPCR Assay

The qPCR was performed on cDNA generated from HCT116, Lovo, and PC3 cells as described in "Example 1". qPCR reactions were carried out in triplicate using the two-step SYBR Green PCR master mix. The expression of exon 2/3 was normalized with house-keep gene GADH also Bax exon 4/5 which is stable in these cells. The data show that the level of exon 2 is lower (19%) in LoVo cells, which are BaxG7/G9 and positive with both Baxd2 and Baxd2G9, While about 40% of the level of exon 2 was detected in PC3, which have a wild type of BaxG8/G8 on both alleles. The results indicate that Bax G8/G8 cells with wild type Bax, have less favorable to process BaxΔ2 splicing in comparison to G7 mini-gene.

Example 3

Validation of the Antibody Against BaxΔ2 Isoform

The anti-BaxΔ2 monoclonal antibodies (mAb) were generated using commercial service (Precision Antibody). Twenty clones were collected and screened. Clone 2D4 was subsequently chosen for all experiments requiring BaxΔ2 antibody. The collection and preparation of clone 2D4 antibody from cultured 2D4 hybridoma were performed according to a standard method. To test the antibody specificity, Bax negative cells, $bax^{-/-}$ MEFs (mouse embryonic fibroblast), which lack bax gene, were transfected with Baxα or BaxΔ2 cDNA plasmids. The cell lysates were prepared and subjected to immunoblotting analysis with BaxΔ2 antibody (2D4). Antibody against Baxα (N20) was used as a control. The BaxΔ2 mAb is specific to the BaxΔ2 protein and does not react with Baxα, and vice versa. Consistent with this, $bax^{-/-}$ MEFs transfected with GFP-tagged Baxα or BaxΔ2 show that the BaxΔ2 antibody is also specific to BaxΔ2 protein in immunostaining. An example of usage of 2D4 antibody in immunohistochemical staining in formalin fixed paraffin embedded (FFPE) tissue sections indicating that there is no positive staining of BaxΔ2 in the tumor which has wild type of Bax microsatellite (G8/G8). However, BaxΔ2 protein expression is detected in Bax (G7/G8) section.

Example 4

Preparation and Validation of the Isogenic BaxΔ2 Sublines

Human colon cancer cell line HCT116 was purchased from ATCC (American Type Culture Collection Cat# CCL247). HCT116 colon cancer cells contain mixed populations with different Bax microsatellite statuses as follows: the majority of these cells (94%) have mixed Bax alleles (G8/G7); 4% of these cells have pure Bax G7/G7; and 2% of these cells have pure Bax G8/G8. Single cell cloning was carried out by serial dilution in a 96-well plate and cultured for 2 to 3 weeks until the single clones were expanded sufficient enough for validation. These single cell-derived isogenic sublines were individually maintained for further usage. The genomic DNA was isolated from each isogenic subline, the Bax microsatellite status was determined by PCR with primers mentioned in "Example 1" and DNA sequence. The subline clone #10 (HCT116-BP10) has Bax (G7/G7), which has mononucleotide deletions in both Bax alleles; the subline clone #28 (HCT116-BN28) contains Bax mixed G7/G8, which has a mononucleotide deletion on one allele of Bax gene. Both clones were selected for further analysis. HCT116-BP10 has a BaxΔ2 alternative splicing product in comparison with the BaxΔ2 positive control. However, HCT116-BN28 has only constitutive splicing product but no detectable BaxΔ2 splicing product. Immunoblotting analysis revealed that the endogenous BaxΔ2 protein levels were extremely low in clone HCT116-BP10 and undetectable in HCT116-BN28. However, BaxΔ2 proteins were easily detected in HCT116-BP10 when the cells were treated with MG-132, a proteasomal inhibitor. Under the same conditions, HCT116-BN28 had no detectable BaxΔ2 proteins. Of note, both clone #10 and clone HCT116-BN28 had no detectable parental Baxα proteins, as analyzed by immunoblotting using several anti-Baxα antibodies. Taken together, these results indicate that cancer cells harboring Bax G7/G7 mutations are capable of generating BaxΔ2 proteins, although the BaxΔ2 proteins appear to be unstable and prone to proteasomal degradation. To analyze the physiological characteristics of these two HCT116 isogenic sublines, the growth rate, invasion ability and colony formation of both clones HCT116-BP10 and HCT116-BN28 cells were analyzed. We found that clones HCT116-BP10 and HCT116-BN28 were quite similar to each other in terms of growth rate and invasive ability. However, the BaxΔ2-positive clone HCT116-BP10 had significantly less capability in colony formation compared with the BaxΔ2-negative clone HCT116-BN28. These results indicate that BaxΔ2-positive cells may be less tumorigenic in tumor development.

Example 5

Usage BaxΔ2 Sub-Lines for Drug Screening

Figure 8:
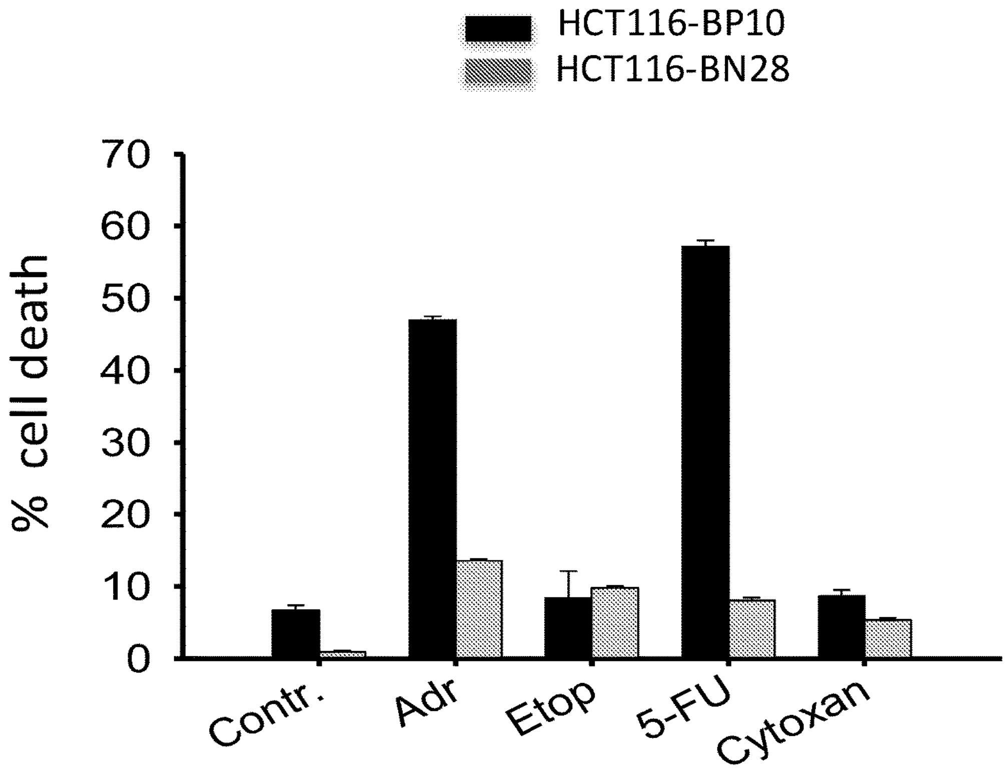
FIG. 8. Cell death assay of HCT116 sublines clone HCT116-BP10 and clone HCT116-BN28) treated with chemotherapeutic drugs as indicated for 36 hours. Adr, Adriamycin; Etop, Etoposide; 5-FU, 5-fluorouracil; Contr, control.

This example related to demonstration of using the BaxΔ2 positive and negative sublines to screen chemo-drugs cytotoxicity. BaxΔ2 positive (HCT116-BP10) and negative (HCT116-BN28) sublines were treated with Adriamycin (40 ug/ml) or 5-FU (500 ug/ml) for 36 hours in a regular cell culture medium. Cell death assay showed that BaxΔ2 positive clone #10 cells are more sensitive to treatment from 5-FU or Adriamycin but not Etoposide and Cytoxan (FIG. 8). Both Adriamycin and Etoposide are in the same category as topoisomerase inhibitors; and both 5-FU and Cytoxan are in the same class of alkaloid drugs. Therefore the result indicates that BaxΔ2 positive cancer cells are selectively sensitive to a subgroup of chemo-drugs.

Example 6

Figure 9:
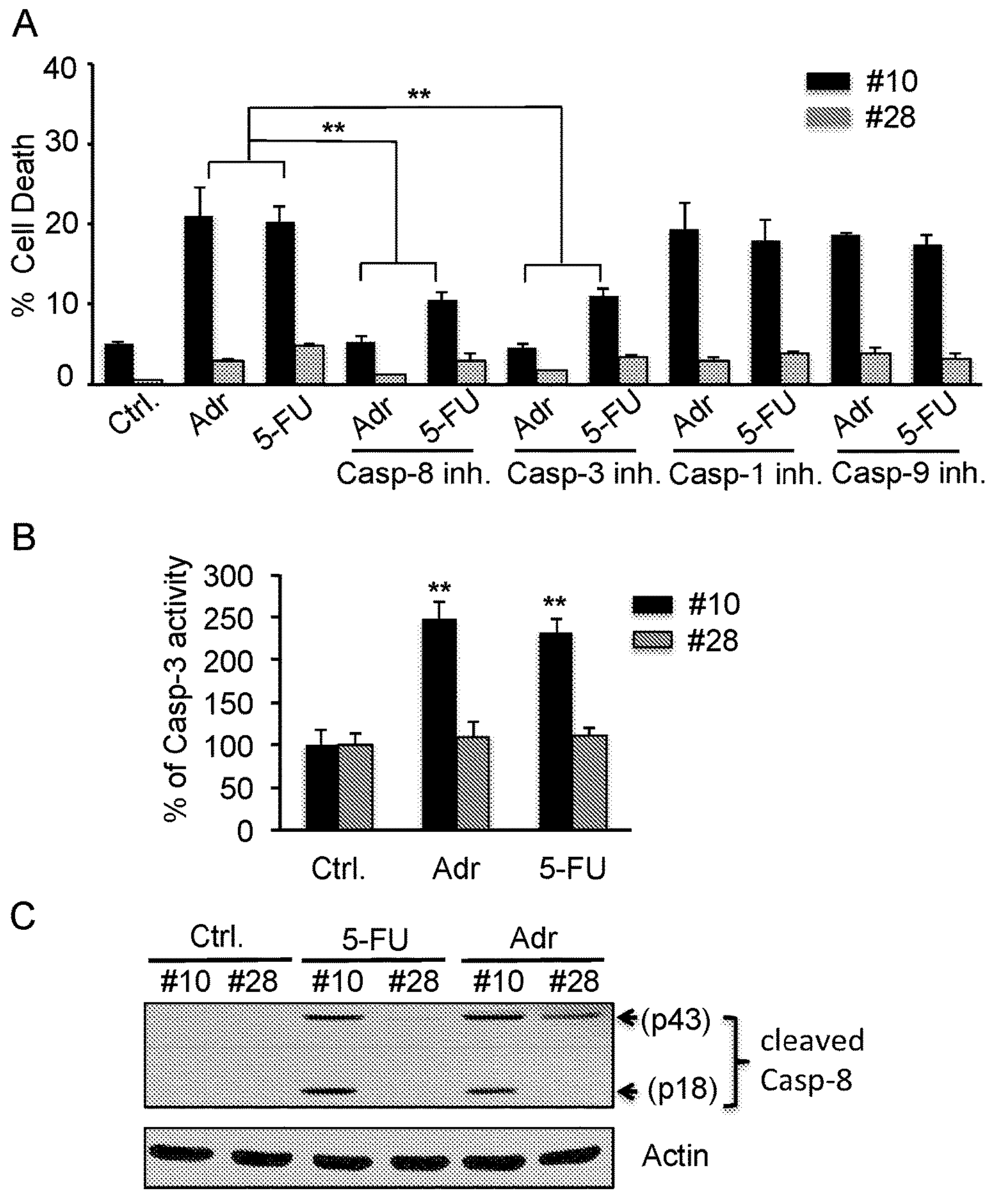
FIG. 9. BaxΔ2 promotes apoptosis through activation of caspase-8. A, Cell death assay of HCT116 clone #10 and clone #28 cells treated with or without 5-FU (500 μM) or Adriamycin (Adr, 4 μg/ml) for 24 h in the presence of inhibitors (50 μM each) for caspase-3 (DEVD) SEQ ID NO: 4), caspase-8 (IETD) (SEQ ID NO: 5), caspase-1 (YVAD) (SEQ ID NO: 6), and caspase-9 (LEHD) (SEQ ID NO: 7) as indicated. ** P<0.01. inh., inhibitor. B, Caspase-3 assay of HCT116 clone #10 and #28 cells treated as described in (A). The activity of caspase-3 was measured using fluorogenic caspase-3 substrate DEVD-AFC (SEQ ID NO: 4) (50 μM) with a microplate spectrofluorometer. C, Immunoblotting analysis for the detection of cleaved casapase-8 in the chemodrug treated clone #10 and #28 cells with an anti-cleaved caspase-8 antibody.
Figure 10:
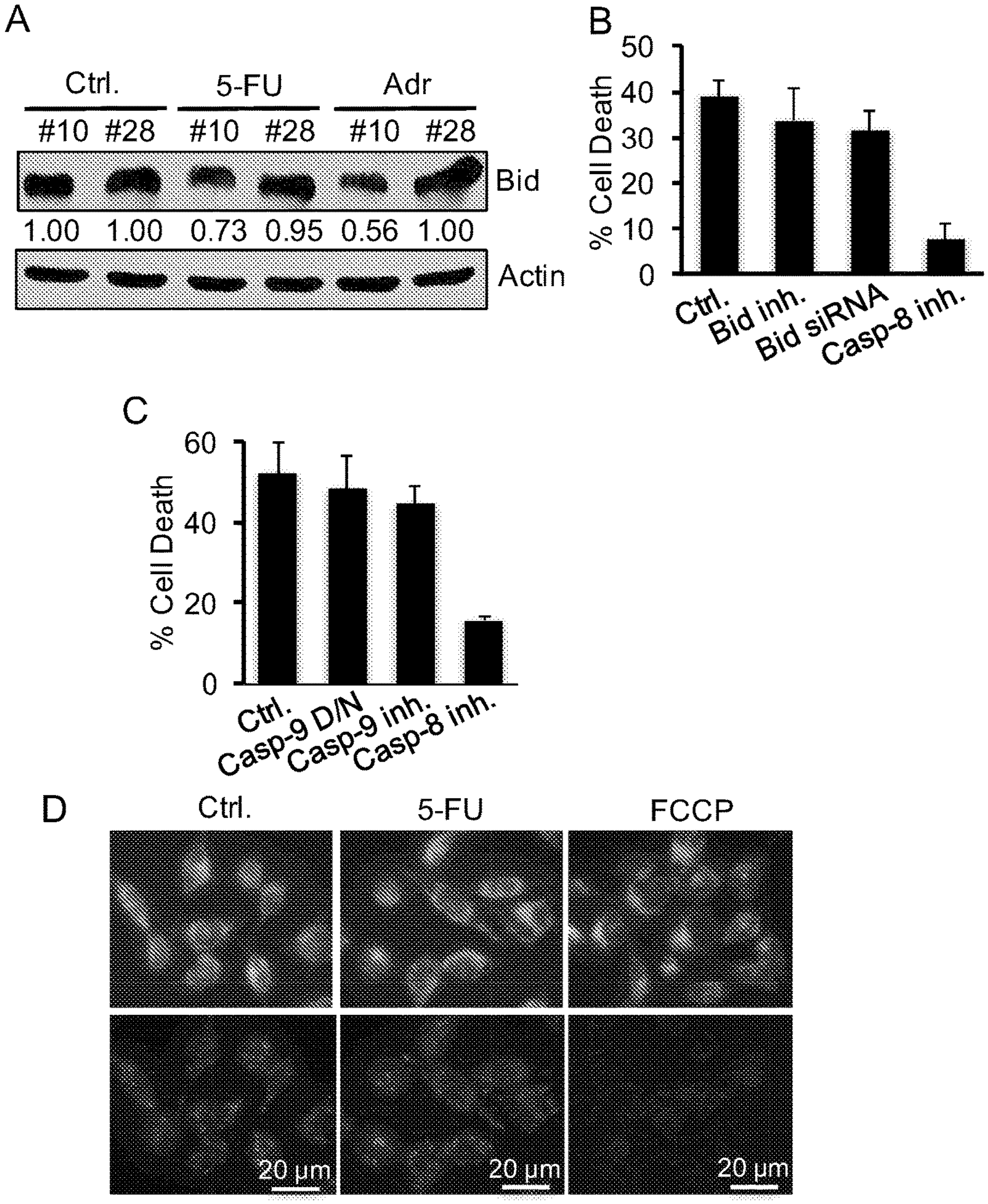
FIG. 10. The Bid-dependent mitochondrial death pathway is not essential for the onset of chemodrug-induced apoptosis in BaxΔ2-positive cells. A, Immunoblotting analysis of cleaved Bid in HCT116 clone #10 and #28 cells treated with or without 5-FU (500 μM) or Adriamycin (4 pg/ml) as indicated. The intensities of truncated Bid bands were quantitated relevant to the actin control and are presented as arbitrary numbers. B, Cell death assay of HCT116 clone #10 cells treated with 5-FU (500 μM) in the presence of a Bid specific inhibitor (BI-6C9; 10 μM) or Bid siRNA. C, Cell death assay of clone #10 cells treated with 5-FU (500 μM) in the presence of a caspase-9 inhibitor (LEHD (SEQ ID NO: 7); 50 μM) or transfected with a caspase-9 dominant negative (D/N) mutant construct. D, Representative images of JC-1 staining. Carbonyl cyanide 4-(trifluoromethoxy) phenylhydrazone (FCCP; 100 μM) was used as a positive control. JC-1 monomer green fluorescence as observed by excitation with 488 nm and emission with 529 nm (top panel). JC-1 aggregate red fluorescence as observed by excitation at 546 nm and emission at 590 nm (bottom panel).

BaxΔ2 Promotes Apoptosis Through Caspase-8 Activation in Microsatellite Unstable Colon Cancer Loss of apoptotic Bax due to microsatellite mutation contributes to tumor development and chemoresistance. As shown in the above examples, a Bax microsatellite mutation was uncovered in combination with a specific alternative splicing event that could generate a unique Bax isoform (BaxΔ2) in otherwise Bax-negative cells. Like the prototype Baxα, BaxΔ2 is a potent pro-apoptotic molecule. However, the pro-apoptotic mechanism and therapeutic implication of BaxΔ2 remain elusive. In this example, the isolation and analysis of isogenic sub-cell lines are described that represent different Bax microsatellite statuses from colorectal cancer. Colon cancer cells harboring Bax microsatellite G7/G7 alleles are capable of producing low levels of endogenous BaxΔ2 transcripts and proteins. Interestingly, BaxΔ2-positive cells are selectively sensitive to a subgroup of chemotherapeutics compared with BaxΔ2-negative cells. Unlike other Bax isoforms, BaxΔ2 recruits caspase-8 into the proximity for activation, and the latter, in turn, activates caspase-3 and apoptosis independent of the mitochondrial pathway (FIGS. 9 and 10). These data suggest that the expression of BaxΔ2 may provide alternative apoptotic and chemotherapeutic advantages for Bax-negative tumors.

Bax is a pro-apoptotic Bcl-2 family member. Typically, Bax promotes apoptosis through the activation of the mitochondrial death pathway. Under a non-stimulated condition, Bax localizes in the cytosol as monomers. Upon stimulation by a death signal, Bax translocates to the mitochondrial membrane where it disrupts the mitochondrial membrane, causes the release of cytochrome C, and sequentially activates caspase-9 and caspase-3 for cell death. Bax has several isoforms, mostly generated by alternative splicing between exon 1 and exon 3 or between exon 5 and exon 6 from the prototype Baxα pre-mRNA. These isoforms either universally exist in normal and cancer cells or are only detectable in certain tissues. The pro-apoptotic activity of Bax isoforms can be well preserved as long as the Bax functional BH domains remain intact. Some of the Bax isoforms, such as Baxβ, change the stability of proteins, while others change their potencies of cell death. Nevertheless, most Bax isoforms promote apoptosis using the same mechanism as the prototype Baxα, i.e., through the activation of the mitochondrial death pathway.

Bax is one of the genes that are frequently mutated in MSI tumors. The inactivation of Bax by a frameshift mutation is found in 50% of HNPCC. The deletion of a single guanine nucleotide (G) in the Bax exon 3 microsatellite tract (from G8 to G7) results in a reading frameshift and "Bax-negative" phenotype due to a premature termination codon. The loss of Bax often promotes tumor growth and increases resistance to chemotherapeutics. It is discovered that the mutation-mediated loss of Bax could be restored by unique alternative splicing that produces a novel Bax isoform, BaxΔ2, which exists only in cells harboring the Bax microsatellite G7 mutation. BaxΔ2 transcripts can be detected in both MSI cancer cell lines and primary tumors. BaxΔ2 is a more potent apoptotic inducer than Baxα. In this example, we show that BaxΔ2 proteins determine the chemosensitivity of colon cancer cells. Unlike Baxα, the pro-apoptotic activity of BaxΔ2 is mediated by the activation of the caspase-8 pathway rather than the mitochondrial death pathway. Our results uncover a distinct mechanism by which BaxΔ2 induces apoptosis and suggest that BaxΔ2 is a potential target for cancer therapy.

Materials and Methods

Materials

Antibody against Bax (N20, against the Bax N-terminus) was purchased from Santa Cruz Biotechnology (Santa Cruz, Calif.). The BaxΔ2 monoclonal antibody was generated as described above. Antibodies against cleaved human specific caspase-8 and mouse specific caspase-8, and human specific Bid were from Cell Signaling Technology (Danvers, Mass.). The antibody against full-length caspase-8 (LS-C99287) was from Lifespan BioSciences (Seattle, Wash.). The pan-Caspase inhibitor (Z-VAD-FMK), Caspase-1 Inhibitor I (Ac-YVAD-CHO) (SEQ ID NO: 6), Caspase-8 Inhibitor II (Z-IETD-FMK) (SEQ ID NO: 5), Caspase-3 Inhibitor II (Z-DEVD-FMK) (SEQ ID NO: 4) and Caspase-9 Inhibitor (Z-LEHD-FMK) (SEQ ID NO: 7) were from Calbiochem (Billerica, Mass.). Adriamycin, Indomethacin, Cyclophosphamide (Cytoxan), Cysplatin (CDDP), Fluorouracil (5-FU), Irinotecan (CPT-11), Vinblastine, and Paclitaxel (Taxol) were from Sigma-Aldrich (St. Louis, Mo.). Etoposide and MG-132 were from Calbiochem (Billerica, Mass.). Hydroxyurea, Daunorubincin and Epirubicin were from Santa Cruz Biotechnology (Dallas, Tex.). Bid specific inhibitor (BI-6C9) was from Sigma-Aldrich. The mitochondrial membrane potential assay kit was from Abcam (Cambridge, Mass.).

Cell Lines and Isogenic Sublines

Colon cancer cell line HCT116 was obtained from American Type Culture Collection. The cell line was tested and authenticated by Genetica (Cincinnati. Ohio) before the experiments. Both HCT116 and $Bax^{-/-}$ mouse embryonic fibroblasts (MEFs) cells were cultured in DMEM supplemented with 10% FBS. To isolate single cell population from HCT116 cells, cells were treated with 500 μM Indomethacin for 72 h to enrich Bax G7 population. Single-cell suspension was plated onto 96-well plates without Indomethacin. Single clones were recovered, expanded, and validated by both genomic sequencing and RT-PCR analysis.

Bax Microsatellite Sequencing and RT-PCR

Genomic DNAs were isolated from different HCT116 sublines with DirectPCR lysis reagent (Viagen Biotech) according to the manufacture's instruction. Microsatellite region of Bax gene was amplified by PCR with specific primers surrounding Bax exon 3 microsatellite region, 5' GAGTGACACCCCGTTCTGAT 3' (SEQ ID NO: 40) (forward) and 5' ACTCGCTCAGCTTCTTGGTG 3' (SEQ ID NO: 41) (reverse). The PCR products were purified by using MinELute PCR purification kit (QIAGEN) and subjected to sequence analysis for determination of the Bax microsatellite status. For RT-PCR, total RNA was isolated using the PureLink RNA Mini kit (Life Technology) according to the manufacture's instruction. The cDNAs were reversely transcribed from mRNA using ThermoScript RT-PCR System (Invitrogen). The transcripts were amplified with Bax primers, 5'-GCT CTA GAG AGC GGC GGT GAT GGA CGG GT-3' (SEQ ID NO: 44) (forward), and 5'-GGA ATT CCA GCT GGG GGC CTC AGC CCA T-3' (SEQ ID NO: 45) (reverse), or BaxΔ2 specific primers, 5'-CCA GAG GCG GGG GGT TTC ATC C-3' (SEQ ID NO: 8) (forward), 5'-GGT TGT CGC CCT TTT CTA CTT TGC CA-3' (SEQ ID NO: 46) (reverse).

Transient Transfection and RNA Interference

Cells were allowed grown in 6-well plates to 70-80% confluences before transfection. Caspase-9 dominant negative construct (LZRS-caspase-9, D/N) and Bid siRNA (5'GGGCAAAAGC UUACAAAUAUU3') (SEQ ID NO: 47), as well as controls, were transfected using lipofectamine 2000 according to the manufacturer's instruction (Life Technology).

Co-Immunoprecipitation and Immunostaining

Cell pellets were lysed in NP-40 buffer (145 mM NaCl, 5 mM MgCl, 1 mM EGTA, 0.25% NP-40, 20 mM HEPES, pH 7.4) with a cocktail of protease inhibitors at 4° C. for 30 min Cell lysates were incubated with the appropriate antibody-conjugated beads overnight at 4° C. The beads were washed with NP-40 buffer for 3 times and the immunocomplexes were separated by SDS-PAGE and subjected to immunoblotting analysis. For immunostaining, cells were grown on cover slips coated with 1% gelatin. Cells were fixed and permeabilized with ice-cold methanol and incubated with primary antibodies diluted in PBS plus 0.3% Triton-X and 3% BSA. Following PBS washing, cells were incubated with Alexa Fluorescence conjugated secondary antibodies. Cell nuclei were stained with DAPI. The fluorescence images were collected by Leica SP5 Laser Scanning Confocal microscope using a 40× objective.

Mitochondrial Membrane Potential Assay

Cells ($5\times10^6$ per well) in 6-well plates were treated with different stimuli for a period of time as indicated in the figure legends. For the positive control, cells were treated with FCCP (Carbonyl cyanide 4-(trifluoromethoxy) phenylhydrazone, 100 μM) for 30 min before staining. Mitochondrial membrane potentials (MMP) were analyzed by using a mitochondrial specific cationic dye (JC-1) according to the manufacturer's instruction and the images were collected by Nikon TE-2000 fluorescence microscope. The quantitation of MMP was performed using ImageJ program with at least 5 random fields for each sample.

Colony Formation and Invasive Assays

A standard colony formation assay was performed. Briefly, total $1.5\times10^4$ cells were seeded in each well in a 6-well plate. After culturing for 3-4 weeks, the colonies were visualized by staining with crystal violet and triplicate samples were counted under the dissecting microscope. The transwell invasion assay was performed by using transwell inserts with 8.0 μm pore size in 6-well plates. Total $5\times10^5$ cells were seeded into the upper chamber and cultured for 24 h. Cells were fixed in the following day with 5% Glutaraldehyde and stained by Toluidine Blue. The inner surface of the upper chamber was carefully wiped using a cotton swab. Invasive cells were counted in three randomly selected fields for each well under a microscope.

Results

Figure 7:
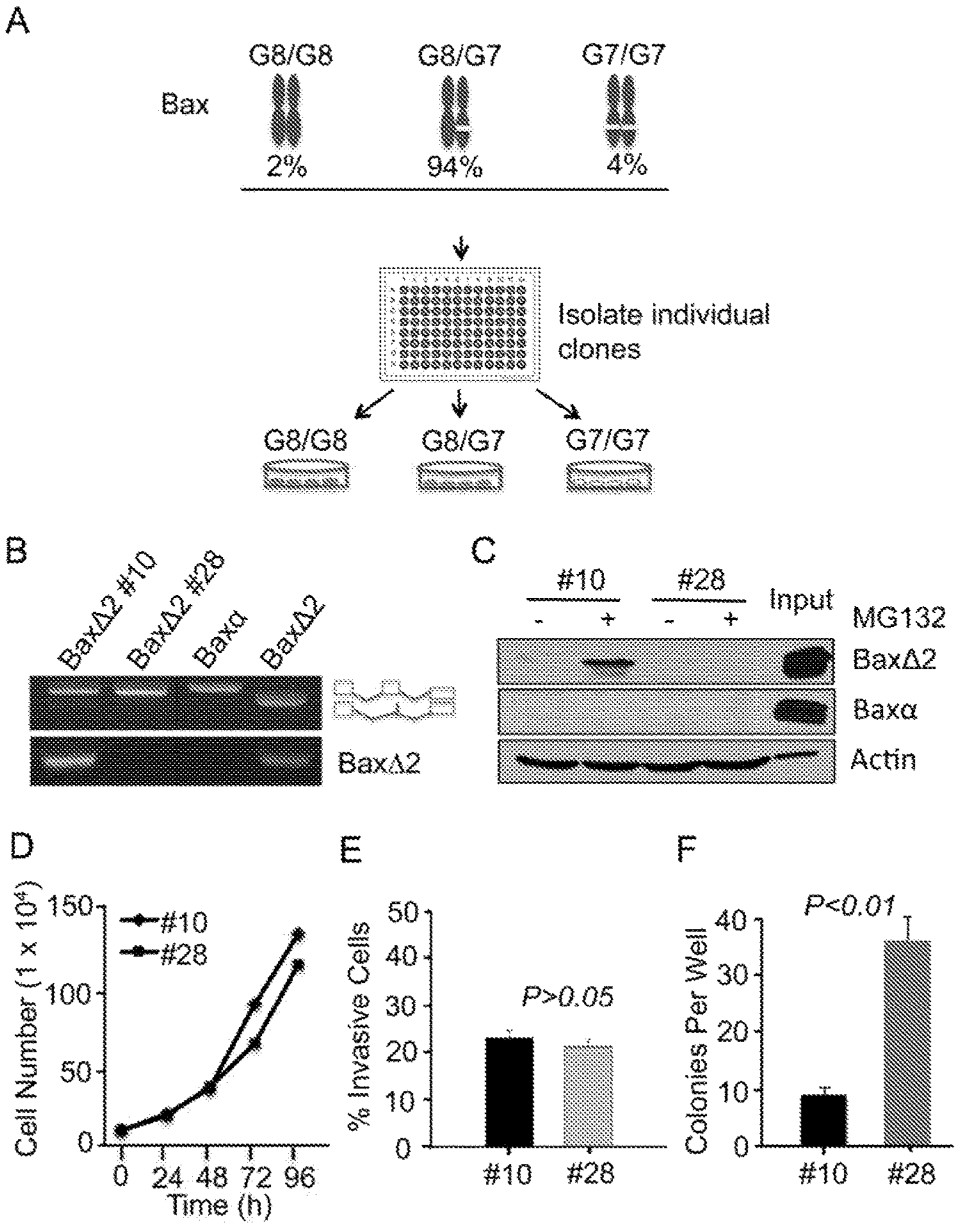
FIG. 7. Generation and characterization of the isogenic subline cells with the different Bax microsatellite status. A, Schematic diagram of generating the HCT116 sublines. Cells were treated with 500 μM Indomethacin for 72 h. A single cell suspension was plated into 96-well plates without Indomethacin. Bax microsatellite statuses (G8/G8, G8/G7, or G7/G7) of each sublines were determined by genomic sequencing as described in the methods. B, RT-PCR analysis of Bax alternative splicing and BaxΔ2 production. The cDNAs were generated from HCT116 clones #10 (G7/G7 genotype) and clone #28 (G8/G7 genotype) with a set of primers that cover Bax exon 1 through exon 6, or primers specific for BaxΔ2 as described in the methods. The PCR products of Baxα and BaxΔ2 plasmid DNA were used as controls. C, Immunoblotting of Baxα and BaxΔ2 proteins with an anti-Bax antibody (N20) or an anti-BaxΔ2 antibody (2D4), respectively, in clones #10 and #28 after treatment with MG-132 (10 μM) for 8 h. Inputs of transfected BaxΔ2 and Baxα were used as positive controls. D, Cell growth curve assay of clone #10 and clone #28. Total 1×104 cells were seeded onto 24-well plates and the cell numbers were counted every 24 h up to 96 h. E, Trans-well invasion assay. F, Colony formation assay. All experiments were performed independently at least three times.

The Expression of BaxΔ2 Proteins can be Detected in Colon Cancer Cells Harboring the Bax Microsatellite G7 Mutation Allele BaxΔ2 is a functional Bax isoform produced by a unique combination of a microsatellite mononucleotide deletion (G8 to G7) in Bax exon 3 and alternative splicing of Bax exon 2, as shown in the above examples. HCT116 colon cancer cells contain mixed populations with different Bax microsatellite statuses as follows: the majority of these cells (94%) have mixed Bax alleles (G8/G7); 4% of these cells have pure Bax G7/G7; and 2% of these cells have pure Bax G8/G8. It has been shown that further deletion of the Bax G8 allele in the Bax G8/G7 cells results in a Bax null phenotype and leads to partial chemoresistance. We speculated that the population of HCT116 cells harboring the Bax G7 mutation is capable of producing BaxΔ2, thus remaining sensitive to chemotherapeutic treatment. To test this scenario, we isolated single-cell populations using a standard 96-well plating method (FIG. 7A). More than 54 isogenic sub-clones were isolated and genotyped. The following 20 sub-clones were further analyzed by both genomic sequence and splicing analyses: 14 clones contained Bax G8/G7; 6 clones contained G7/G7; and none of the clones contained G8/G8 (Table 4). Interestingly, all 6 Bax G7/G7 clones contained both detectable transcript products from constitutive splicing and alternative splicing, as determined by RT-PCR (Table 4). In contrast, all Bax G8/G7 clones contained only constitutive splicing transcripts, and none of these clones contained a detectable product from alternative splicing (Table 4). These results suggest that not all alleles containing Bax microsatellite mutations are capable of alternative splicing.

TABLE 4

Analysis the Bax MSI and splicing statuses in HCT116 isogenic sub-cell lines

| Clone# | Bax MSI Status | Splicing |
|---|---|---|
| 3 | G8/G7 | Constitutive |
| 10 | G7/G7 | Constitutive, Alternative |
| 11 | G8/G7 | Constitutive |
| 20 | G7/G7 | Constitutive, Alternative |
| 22 | G7/G7 | Constitutive, Alternative |
| 24 | G8/G7 | Constitutive |
| 28 | G8/G7 | Constitutive |
| 32 | G8/G7 | Constitutive |
| 37 | G8/G7 | Constitutive |
| 38 | G8/G7 | Constitutive |
| 39 | G8/G7 | Constitutive |
| 40 | G8/G7 | Constitutive |
| 41 | G8/G7 | Constitutive |
| 42 | G8/G7 | Constitutive |
| 44 | G7/G7 | Constitutive, Alternative |
| 48 | G8/G7 | Constitutive |
| 49 | G8/G7 | Constitutive |
| 50 | G7/G7 | Constitutive, Alternative |
| 52 | G7/G7 | Constitutive, Alternative |
| 54 | G8/G7 | Constitutive |

To study the ability of the isogenic cells to generate BaxΔ2 transcripts, we further analyzed HCT116 sublines, namely clone #10 (Bax G7/G7) and clone #28 (Bax G8/G7). RT-PCR analysis with primers in Bax exons 1 and 3 revealed that clone #10 (Bax G7/G7) contained both constitutive splicing (upper band) and alternative splicing (lower band), although the constitutive splicing product was predominant (FIG. 7B). In contrast, clone #28 (Bax G8/G7) only contained constitutive splicing products, albeit the Bax G7 mutated allele. Furthermore, only less than 20% of the total pre-mRNA from the Bax G7/G7 population went through the exon 2 alternative splicing (FIG. 7B). To further confirm that the alternative splicing product (lower band) was a BaxΔ2 transcript, the lower band was excised and subjected to sequence analysis. In addition, the BaxΔ2 specific 5' primer covering the junction of exons 1 and 3 was used in the PCR analysis. As expected, the BaxΔ2 transcript was only detected in clone #10 and the BaxΔ2 positive control, but it was not detected in clone #28 and the Baxα negative control (FIG. 7B). Thus, BaxΔ2 transcripts can be easily detected in cells containing the Bax G7/G7 allele.

We then determined the expression of endogenous BaxΔ2 proteins in the HCT116 clones #10 and #28 subline cells using a specific anti-BaxΔ2 antibody. Immunoblotting analysis revealed that the endogenous BaxΔ2 protein levels were extremely low in clone #10 and undetectable in clone #28 (FIG. 7C). However, BaxΔ2 proteins were easily detected in clone #10 when the cells were treated with MG-132, a proteasomal inhibitor (FIG. 7C). Under the same conditions, clone #28 had no detectable BaxΔ2 proteins. This result was consistent with previous observations (FIG. 7B) that Bax G8/G7 cannot generate detectable BaxΔ2 transcript and protein. Of note, both clone #10 and clone #28 had no detectable parental Baxα proteins, as analyzed by immunoblotting using several anti-Baxα antibodies (FIG. 7C and data not shown). Taken together, these results indicate that cancer cells harboring Bax G7/G7 mutations are capable of generating BaxΔ2 proteins, although the BaxΔ2 proteins appear to be unstable and prone to proteasomal degradation.

To analyze the physiological characteristics of these two HCT116 isogenic sublines, the growth rate, invasion ability and colony formation of both clones #10 and #28 cells were analyzed. We found that clones #10 and #28 were quite similar to each other in terms of growth rate (FIG. 7D) and invasive ability (FIG. 7E). However, the BaxΔ2-positive clone #10 had significantly less capability in colony formation compared with the BaxΔ2-negative clone #28 (FIG. 7F). These results indicate that BaxΔ2-positive cells may be less tumorigenic in tumor development.

BaxΔ2-Positive Subline Cells are Sensitive to a Subgroup of Chemotherapeutics

We have previously shown that cancer cells with Bax microsatellite mutations, such as prostate cancer 104-R cells (G7/G7) and colon cancer LoVo cells (G7/G9), are more sensitive to Adriamycin treatment than cancer cells with wild type Bax. However, the heterogeneity of different cell lines often adds complexity to data interpretation. To address this issue, we compared HCT116 isogenic subline clone #10 (BaxΔ2-positive) and clone #28 (BaxΔ2-negative) cells for their sensitivities to chemotherapeutic agents. For the initial screening, we selected a panel of different classes of commonly used chemotherapeutic drugs. Cells were treated with a series of doses of each drug, and the results of cell death are shown in Table 5. BaxΔ2-positive clone #10 was more sensitive to Adriamycin than BaxΔ2-negative clone #28, which was consistent with the previous report that BaxΔ2-positive cancer cells are more sensitive to Adriamycin than BaxΔ2-negative cancer cells. In addition, BaxΔ2-positive clone #10 was also highly sensitive to 5-FU, a pyrimidine analogue compared with the BaxΔ2-negative clone #28 (Table 5). These data indicate that BaxΔ2-positive cells may have a therapeutic advantage or preference to a subgroup of chemotherapeutic drugs.

TABLE 5

Initial screening for chemo-sensitiveies in the HCT116 isogenic sub-cell lines

| | | Chemo-sensitivity | |
|---|---|---|---|
| Class | Name | BaxΔ2+ | BaxΔ2− |
| Alkylating | Cytoxan | ns | ns |
| | Cysplatin (CDDP) | ns | ns |
| Antimetabolites | 5-FU | +++ | + |
| | Hydroxyurea | +++ | ++ |
| Antibiotics | Doxorubicin | +++ | + |
| | Daunorubicin | ns | ns |
| | Epirubicin | +++ | ++ |
| Topoisomerase | Etoposide | ns | ns |
| inhibitor | Irinotecan(CPT-11) | ++ | + |
| Akaloids | Taxol | ns | ns |
| | Vinblastine | ns | ns |

Note:
Cell viability was determined at 48 h post-treatment. +, less 20%, ++, 30-50%, +++ >60%, ns, no significant difference between the BaxΔ2+ and BaxΔ2− groups.

BaxΔ2 Promotes Apoptosis Through Activation of the Caspase-8 Pathway

Bax typically targets the mitochondria upon activation and results in the activation of the caspase-9 and caspase-3 cascade for cell death. To determine the underlying mechanism by which BaxΔ2 promoted cell death, HCT116 clones #10 and #28 were treated with Adriamycin or 5-FU in the presence of different caspase inhibitors. We found that the chemodrug-induced apoptosis was significantly augmented in clone #10 and could be effectively inhibited by either a caspase-8 or caspase-3 inhibitor, but not caspase-1 or caspase-9 inhibitor (FIG. 9A). The caspase-3 activity was confirmed by the caspase-3 fluorometric assay (FIG. 9B). The activation of caspase-3 was not surprising, because it is an executioner caspase downstream of many caspase-mediated cell death events, including the Bax mitochondrial death pathway. However, the activation of caspase-8 was unexpected, as the Bax family usually utilizes the mitochondrial death pathway. Consistent with this notion, immunoblotting analysis using an anti-active caspase-8 antibody revealed that caspase-8 was activated, as indicated by the appearance of the cleaved caspase-8 fragments (43 kDa and 18 kDa), in clone #10 when treated with Adriamycin or 5-FU but not in clone #28 (FIG. 9C). Thus, BaxΔ2 promoted apoptosis through the activation of caspase-8 and its downstream executioner caspase-3.

Activation of the Bid Mitochondrial Pathway is not Essential for the Onset of BaxΔ2-Induced Apoptosis Caspase-8 is one of the initiator caspases in the extrinsic death receptor pathway. Once activated, caspase-8 directly activates the executioner caspase-3, or cleaves the BH-3-only protein Bid into tBid, which in turn targets mitochondria and triggers the release of cytochrome c for apoptosis. We next determined if the Bid-dependent mitochondrial death pathway was required for BaxΔ2 to promote apoptosis. We found that Bid was partially degraded in the BaxΔ2-positive clone #10 cells treated with 5-FU or Adriamycin but not in the BaxΔ2-negative clone #28 cells (FIG. 10A). However, inhibition of Bid activity by its specific siRNA or inhibitor did not significantly affect the chemodrug-induced apoptosis (FIG. 10B). Similar results were obtained using a caspase-9 inhibitor or ectopic expression of the caspase-9 dominant negative mutant (FIG. 10C). Furthermore, caspase-8 was activated as early as 8 h and reached to its maximum activity by 16 h, but the mitochondria membrane potential remained reasonable intact 24 h post-treatment, as evidenced by simultaneously monitoring the caspase activity and mitochondrial membrane potential (FIG. 10D). Taken together, these data indicate that the Bid-dependent mitochondrial death pathway may not be essential for the onset of chemodrug-induced apoptosis in the BaxΔ2-positive cells. Direct activation of caspase-3 by caspase-8 is likely required for the onset of the apoptosis.

BaxΔ2 Activates Caspase-8 by Recruiting it into Proximity

Figure 11:
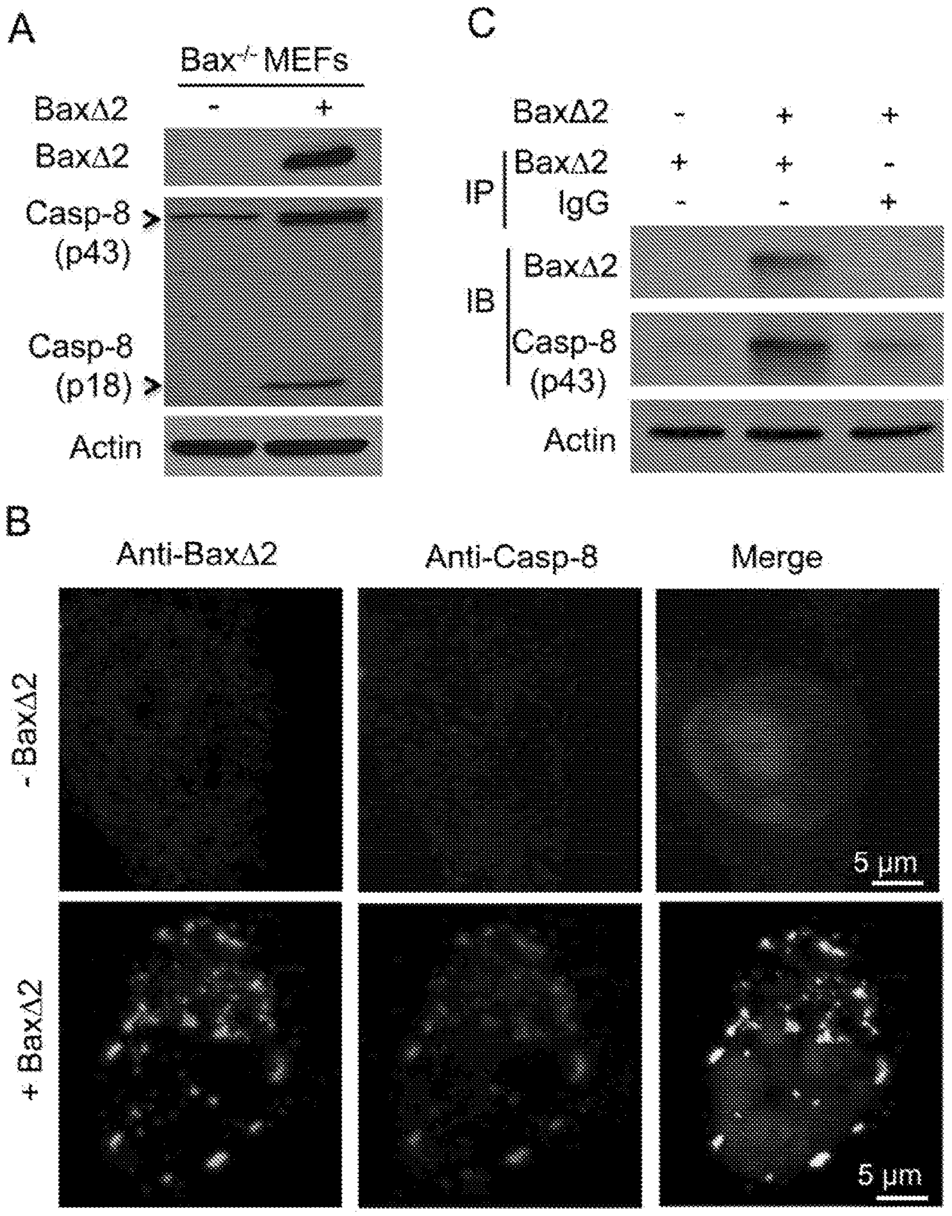
FIG. 11. BaxΔ2 activates caspase-8 through physical interaction. A, Bax−/− MEFs were transfected with BaxΔ2 for 16 h, and the cleavage of caspase-8 was confirmed by immunoblotting with anti-cleaved caspase-8 antibody. B, Cells from (a) were immunostained with an anti-BaxΔ2 (green) and anti-cleaved caspase-8 antibodies (red), and they were imaged using a confocal microscope. Nuclei were stained with DAPI (blue). C, Cells from clone #28 were transfected with BaxΔ2 for 16 h and subjected to immunoprecipitation (IP) with a BaxΔ2 antibody or control IgG. The immunocomplexes were analyzed by immunoblotting (IB) with anti-caspase-8 and anti-BaxΔ2 antibodies. Actin was used as an input control.

Caspase-8 is usually activated by death receptor-mediated self-processing, i.e., the proximity-induced dimerization, followed by aggregation and self-cleavage/activation. We speculated whether BaxΔ2 oligomers or aggregates might serve as a platform to recruit caspase-8 into the proximity for activation. To test this hypothesis, we first examined whether BaxΔ2 and caspase-8 were localized together. Bax null mouse embryonic fibroblast (MEFs) were transfected with BaxΔ2 and the activation of caspase-8 was confirmed by immunoblotting analysis with an anti-cleaved caspase-8 antibody (FIG. 11A) Immunostaining showed that in the absence of BaxΔ2, the staining of caspase-8 was weak and appeared as diffused fine granules (FIG. 11B, top panel). Upon the expression of BaxΔ2, caspase-8 became aggregated and co-localized with BaxΔ2 (FIG. 11B, bottom panel). To determine whether BaxΔ2 and caspase-8 physically interacted with each other, we transfected BaxΔ2 into BaxΔ2-negative HCT116 clone #28 cells. Co-immunoprecipitation in combination with immunoblotting analysis revealed that the amount of the caspase-8 cleaved fragment (p43) was significantly higher in the immunocomplex with the anti-BaxΔ2 antibody than that with the IgG control (FIG. 11C). These data suggest that BaxΔ2 oligomers may serve as a platform for caspase-8 aggregation and activation.

Bax is a pro-apoptotic tumor suppressor and is expressed in almost all types of human cells. Exon 3 of Bax contains a microsatellite sequence that is prone to mutation due to replication slippage if the mismatch repair system is impaired. A single guanine nucleotide deletion from G8 to G7 is the most common mutation in colorectal cancer with microsatellite instability, thus resulting in an apparent Bax null phenotype. Interestingly, alternative splicing of Bax exon 2 can rescue the frameshift mutation, generating a unique and functional BaxΔ2 isoform. In this report, we demonstrated that cancer cells harboring Bax G7/G7 alleles were capable of producing BaxΔ2 transcripts and proteins, although the levels of BaxΔ2 transcripts and proteins were extremely low and unstable (FIGS. 7B and C). BaxΔ2-positive cells were selectively sensitive to a subgroup of chemotherapeutics, such as 5-FU and Adriamycin (Table 5 and FIGS. 9A-C). Surprisingly, BaxΔ2-promoted-apoptosis relied on the activation of caspase-8 and downstream caspase-3 (FIGS. 9A-C). The Bid-mitochondrial pathway appeared not essential for onset of the apoptosis (FIGS. 10A-E). The mechanism underlying caspase-8 activation by BaxΔ2 was most likely through physical interactions between BaxΔ2 and caspase-8 resulting in the formation of aggregates thereby triggering the apoptotic process (FIGS. 11A-C).

There are two criteria in the generation of BaxΔ2. First, the Bax gene must have the deletion of a single guanine nucleotide (G8 to G7) in its exon 3 microsatellite tract. Second, the alternative splicing machinery needs to be able to remove most of exon 2. Previously, we have shown that the alternative splicing factors for BaxΔ2 are universal because cancer or non-cancerous, human or murine fibroblast cells are all able to process the BaxΔ2 alternative splicing in a mini-gene assay. Thus, any Bax G7 allele, theoretically, is able to generate BaxΔ2. However, our current results showed that BaxΔ2 transcripts and proteins were only detected in cells harboring the Bax G7/G7 alleles (FIG. 7B). Furthermore, only less than 20% of total pre-mRNA from the Bax G7/G7 population went through exon 2 alternative splicing (FIG. 7B). Neither alternative splicing nor the BaxΔ2 protein was detected in all Bax G8/G7 subclones tested (Table 4). However, the underlying mechanism is not known. One possibility is that the amount of BaxΔ2 generated by Bax G8/G7 is too low to be detected. Another possibility is that there is a potential inhibitory mechanism for alternative splicing to occur in Bax G8/G7 cancer cells. Future studies are needed to test these possibilities.

Bax usually promotes apoptosis through activation of the intrinsic mitochondria death pathway. Unlike Baxα and other known Bax isoforms, BaxΔ2 lacks exon 2, which is critical for the mitochondria targeting. Although ectopically expressed BaxΔ2 is able to activate the mitochondrial death pathway, it does not mean that BaxΔ2 directly targets mitochondria. Our results indicate that caspase-8 via caspase-3 is essential for the onset of BaxΔ2-induced apoptosis, and that mitochondria may act as an amplifier for the death process. Future studies are needed to explore whether this unique pro-apoptotic feature of BaxΔ2 is related to its ability to sensitize some "Bax-negative" MSI tumor cells to a subgroup of chemotherapeutic drugs.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed here. For example, the terms "comprising", "including," containing," etc. shall be read expansively and without limitation. Additionally, the terms and expressions employed here have been used as terms of description and not of limitation; hence, the use of such terms and expressions does not evidence and intention to exclude any equivalents of the features shown and described or of portions thereof. Rather, it is recognized that various modifications are possible within the scope of the disclosure claimed.

By the same token, while the present disclosure has been specifically disclosed by preferred embodiments and optional features, the knowledgeable reader will apprehend modification, improvement and variation of the subject matter embodied here. These modifications, improvements and variations are considered within the scope of the disclosure.

The disclosure has been described broadly and generically here. Each of the narrower species and subgeneric groupings falling within the generic disclosure also form part of the disclosure. This includes the generic description of the disclosure with a proviso or negative limitation removing any subject matter from the genus, regardless of whether or not the excised material is described specifically.

Where features or aspects of the disclosure are described by reference to a Markush group, the disclosure also is described thereby in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Although the disclosure has been described in conjunction with the above-mentioned embodiments, the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method for treating colorectal cancer, comprising identifying a colorectal cancer patient that contains a cancer cell that expresses a BaxΔ2 protein (SEQ ID NO. 2), and administering to the patient a chemotherapeutic agent that is capable of activating caspase 8, wherein the chemotherapeutic agent is not doxorubicin.

2. The method of claim 1, wherein the chemotherapeutic agent is an antimetabolite.

3. The method of claim 2, wherein the antimetabolite is a pyrimidine analog.

4. The method of claim 2, wherein the antimetabolite is selected from the group consisting of 5-fluorouracil, hydroxyurea, doxifluridine, Capecitabine, tegafur, raltitrexed, nolatrexed, LY231514, ZD9331 and combination thereof.

5. The method of claim 4, wherein the antimetabolite is 5-fluorouracil or hydroxyurea.

6. The method of claim 1, wherein the colorectal cancer is colon cancer.

7. The method of claim 1, further comprising detecting the expression of the BaxΔ2 protein in a cancer cell isolated from the patient.

8. The method of claim 7, wherein the detection uses an antibody having specificity to the BaxΔ2 protein.

9. The method of claim 7, wherein the detection comprises detecting a RNA sequence encoding the BaxΔ2 protein.

10. The method of claim 9, wherein the RNA sequence comprises SEQ ID NO. 1.

11. A method for treating colorectal cancer, comprising administering to a colorectal cancer patient an effective amount of 5-fluorouracil or hydroxyurea, wherein the patient is diagnosed to express a BaxΔ2 protein (SEQ ID NO. 2) in cancer cells.

* * * * *